(12) United States Patent
Schiefer et al.

(10) Patent No.: US 8,987,480 B2
(45) Date of Patent: Mar. 24, 2015

(54) PROCESS OF SEPARATING CHIRAL ISOMERS OF CHROMAN COMPOUNDS AND THEIR DERIVATIVES AND PRECURSORS

(75) Inventors: Gerhard Schiefer, Basel (CH); Thomas Netscher, Basel (CH); Alexander Lucia Leonardus Duchateau, Delft (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 14/116,880

(22) PCT Filed: May 8, 2012

(86) PCT No.: PCT/EP2012/058415
§ 371 (c)(1),
(2), (4) Date: Feb. 10, 2014

(87) PCT Pub. No.: WO2012/152779
PCT Pub. Date: Nov. 15, 2012

(65) Prior Publication Data
US 2014/0155636 A1     Jun. 5, 2014

(30) Foreign Application Priority Data
May 10, 2011   (EP) ..................... 11165442

(51) Int. Cl.
| C07D 311/76 | (2006.01) |
| C07D 311/04 | (2006.01) |
| C07B 55/00  | (2006.01) |
| C07B 57/00  | (2006.01) |
| C07D 311/22 | (2006.01) |
| C07D 311/72 | (2006.01) |

(52) U.S. Cl.
CPC .............. *C07D 311/04* (2013.01); *C07B 55/00* (2013.01); *C07B 57/00* (2013.01); *C07D 311/22* (2013.01); *C07D 311/72* (2013.01)
USPC ........................... 549/401; 549/381; 549/399

(58) Field of Classification Search
CPC ........................... A61K 31/352; C07D 311/76
USPC .......... 549/356, 381, 399, 401; 514/449, 451, 514/456, 458
See application file for complete search history.

(56) References Cited

U.S. PATENT DOCUMENTS 5,744,483 A  *  4/1998  Butler et al. .................. 514/320
7,696,364 B2 *  4/2010  Bonrath et al. ............... 549/411

OTHER PUBLICATIONS

Jensen, S.K., α-Tocopherol Stereoisomers, Vitamins and Hormones, vol. 76, (2007), pp. 281-308.
Abel, et al., "Less Common Applications of Enantioselective HPLC Using the SMB Technology in the Pharmaceutical Industry", in: Ganapathy Subramanian: "Chiral Separation Techniques", vol. 3rd Ed., (Jul. 20, 1997), pp. 251-264.

* cited by examiner

*Primary Examiner* — Golam M M Shameem
(74) *Attorney, Agent, or Firm* — Nixon & Vanderhye P.C.

(57) ABSTRACT

The present invention relates to a process of separating chiral isomers of chroman compounds, particularly tocopherols and tocotrienols as well as the esters and intermediates thereof. It has been found that this process allows a separation of the desired isomer with a higher yield and enables the use of the non-desired isomers in a very efficient way. Said process is particularly useful when implemented in an industrial process. Furthermore, it has been found that this process allows using isomer mixtures as they result from traditional industrial synthesis.

26 Claims, 18 Drawing Sheets

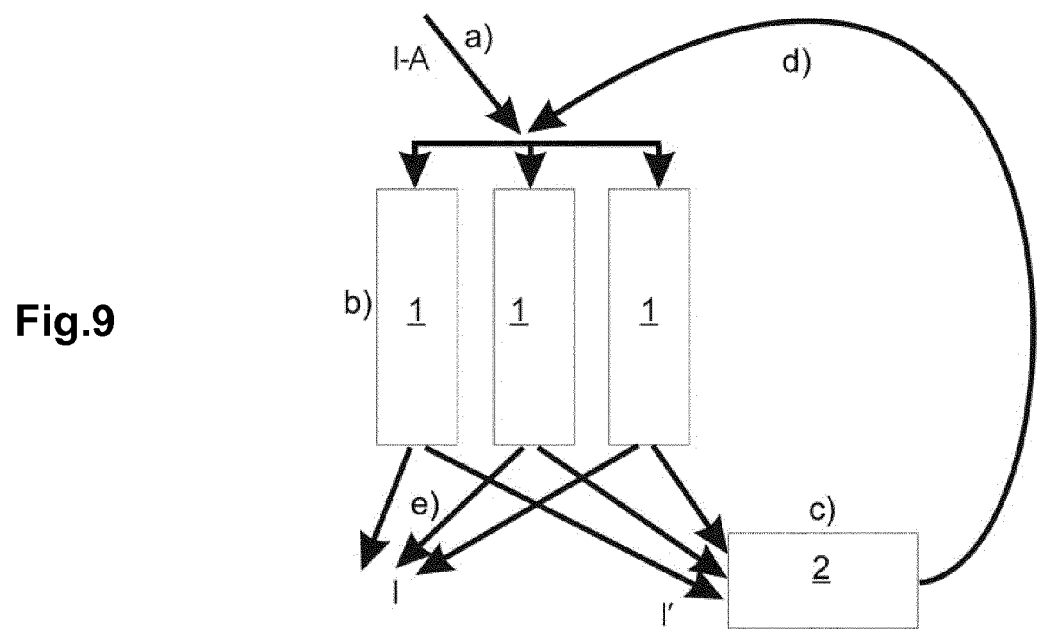
Fig. 9
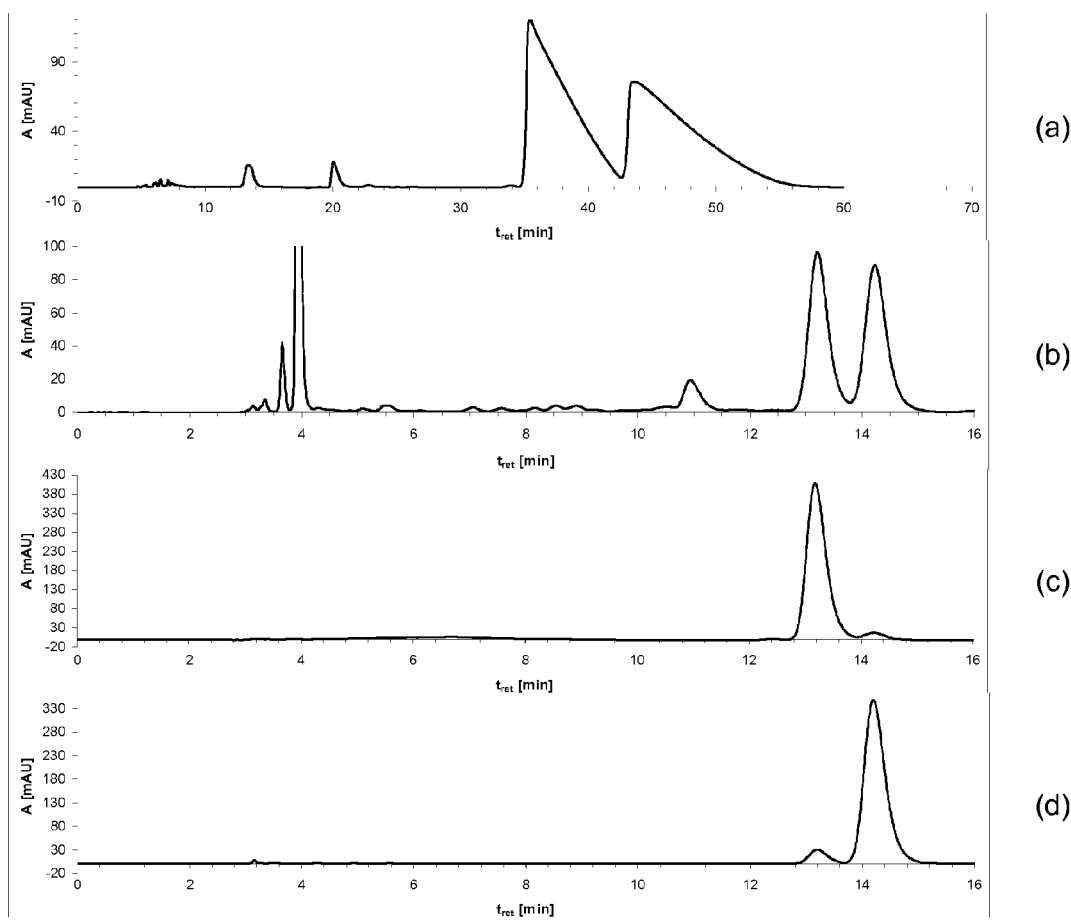
Fig. 10 Chromatograms of separation of (RS)-6-hydroxy-2,5,7,8-tetramethyl-2-((3E,7E)-4,8,12-trimethyltrideca-3,7,11-trienyl) chroman-4-one

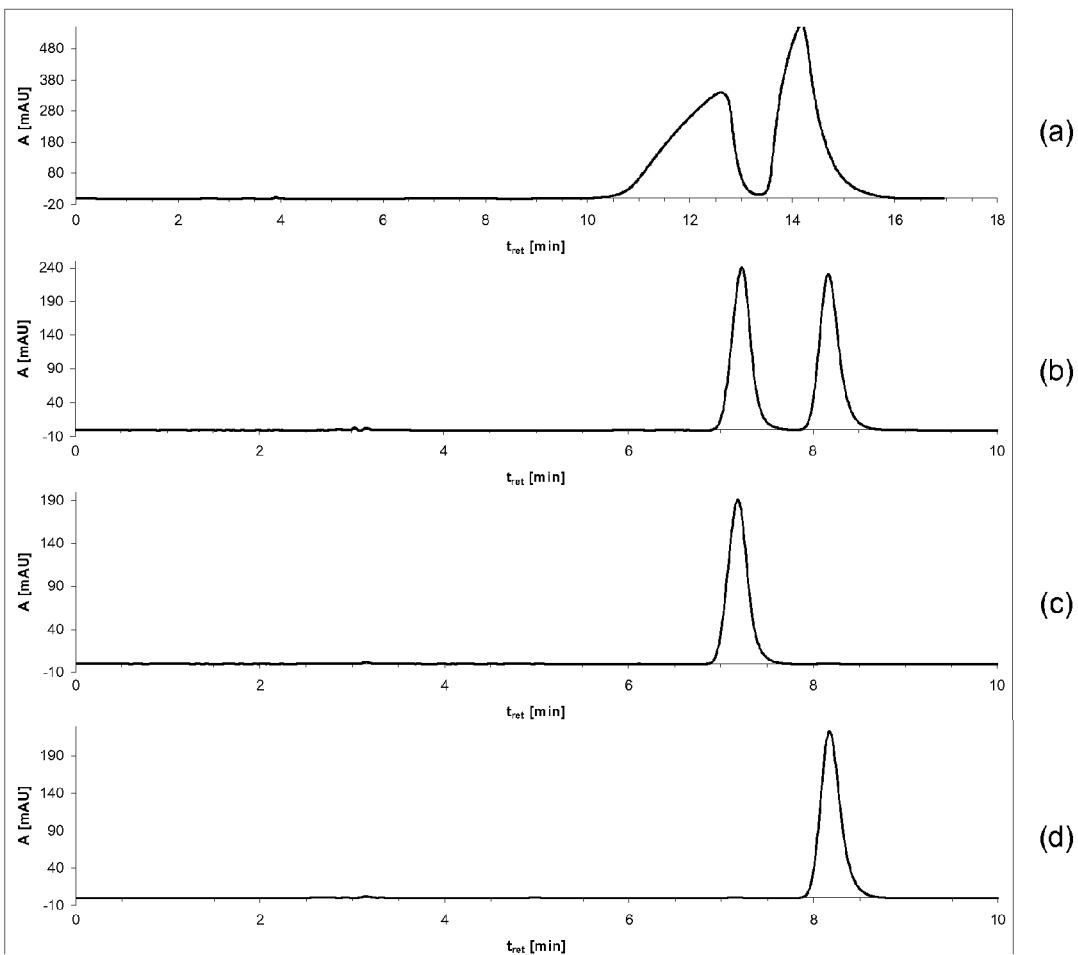
Fig. 11 Chromatograms of separation of (all-*rac*)-α-tocopherol.
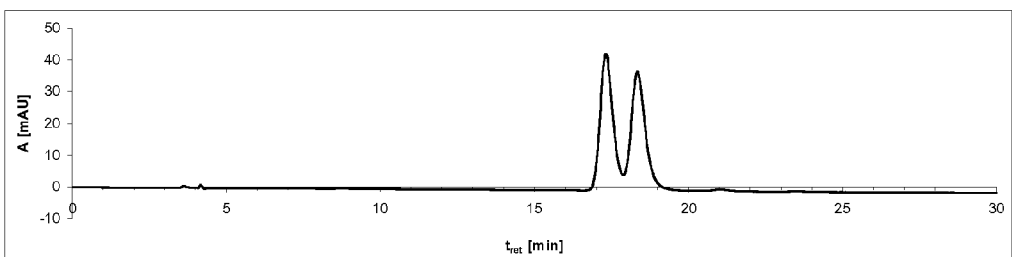
Fig. 13 Chromatogram of (2R,4'R,8'R)-γ-tocopherol after isomerization

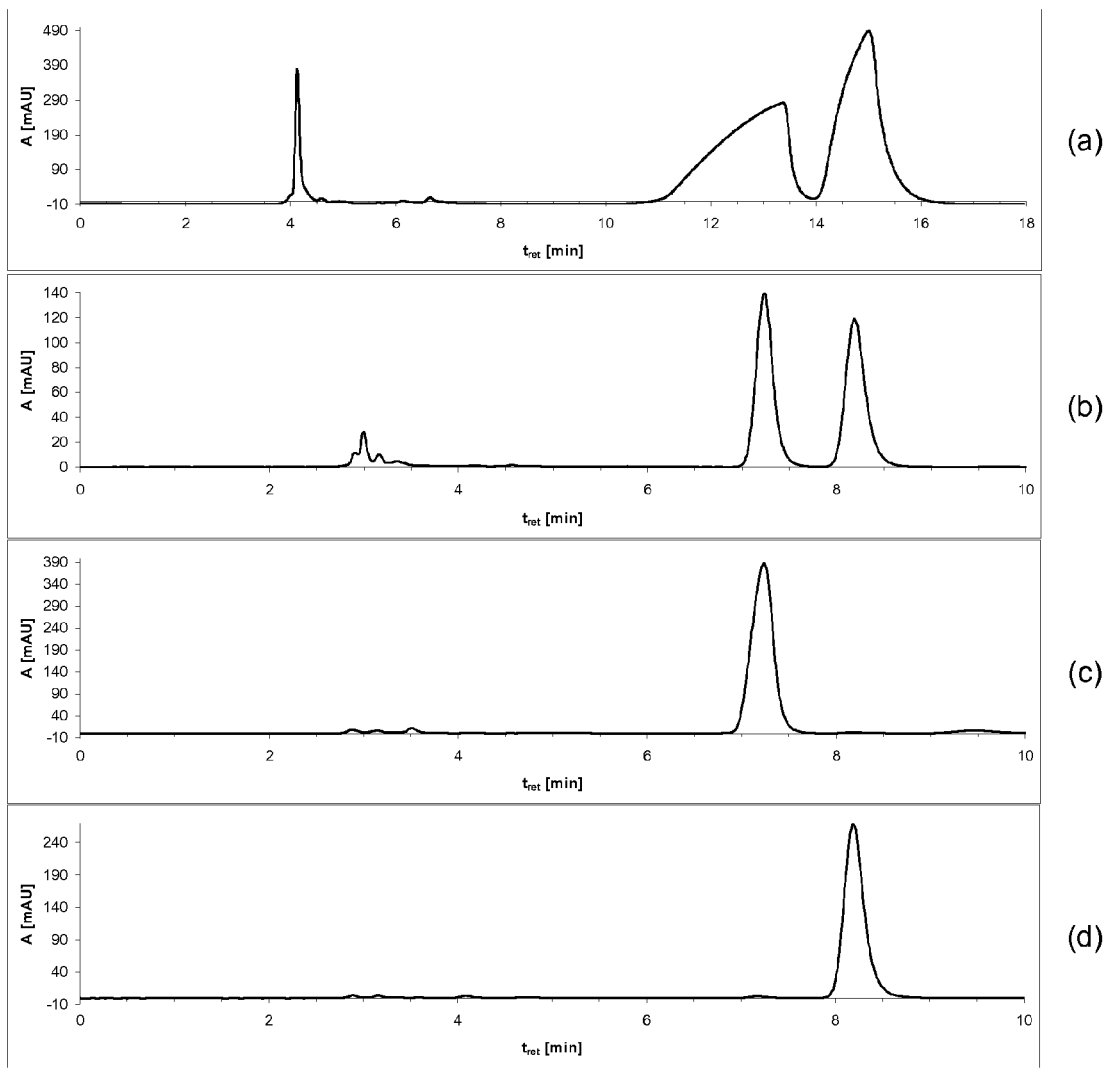
Fig. 12 Chromatograms of separation of 2-*ambo*-α-tocopherol
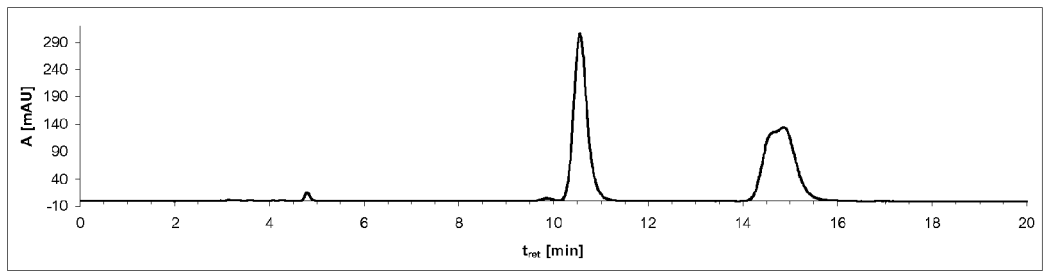
Fig. 14 Chromatogram of (2R,4'R,8'R)-3,4-dehydro-α-tocopherol after isomerization

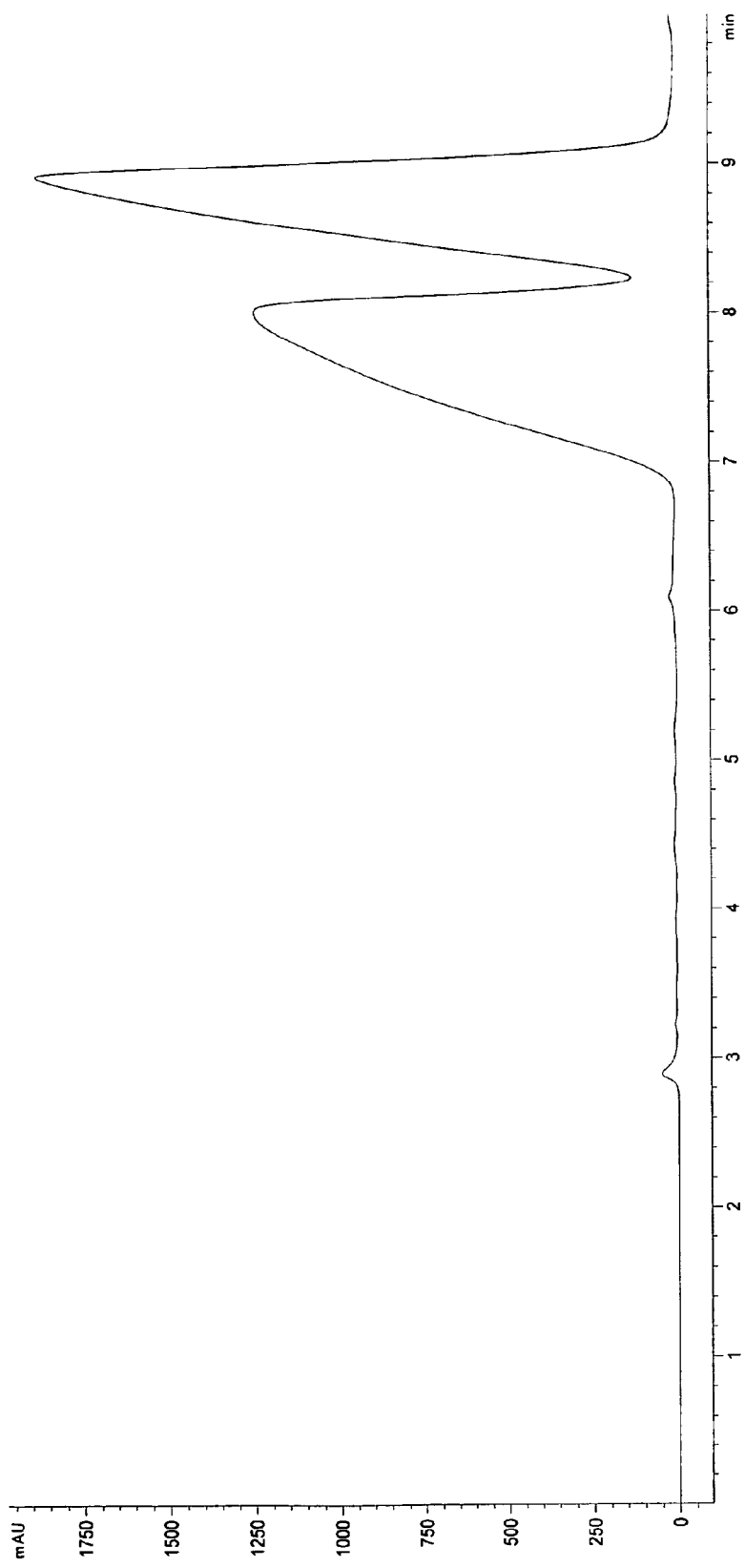
Fig. 15 a) Chromatograms using different alcohols: Eluent: hexane / ethanol

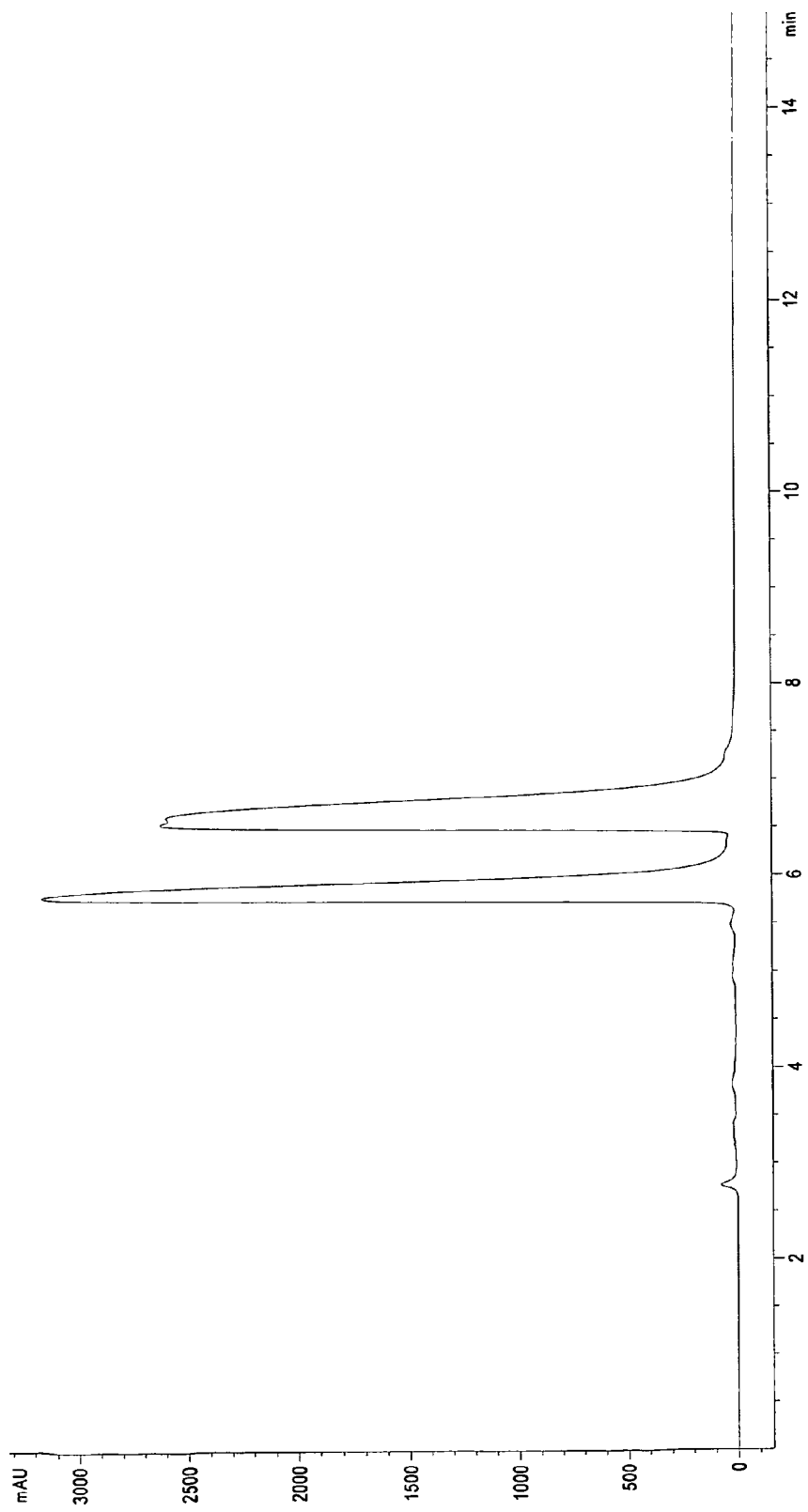
Fig. 15 b) Chromatograms using different alcohols: Eluent: hexane / isopropanol

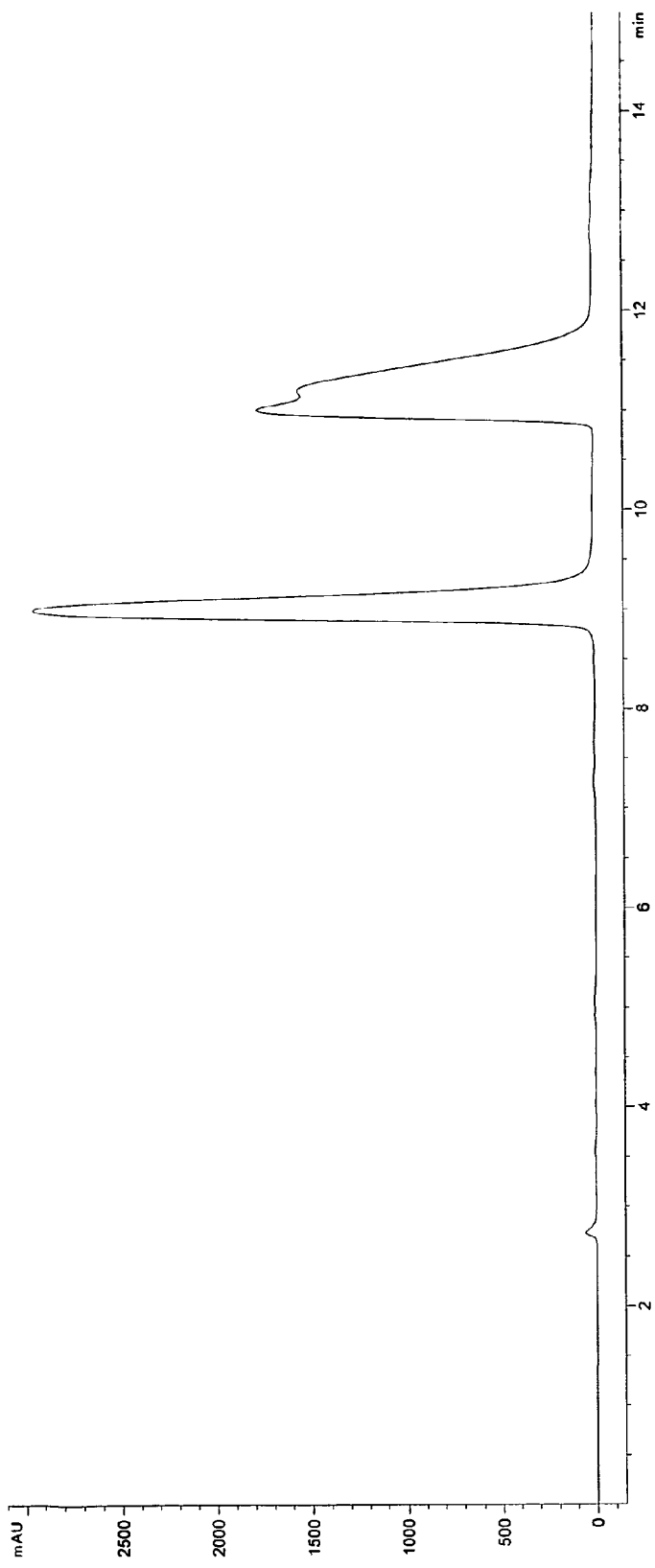
Fig. 15 c) Chromatograms using different alcohols: Eluent: hexane / 1-propanol

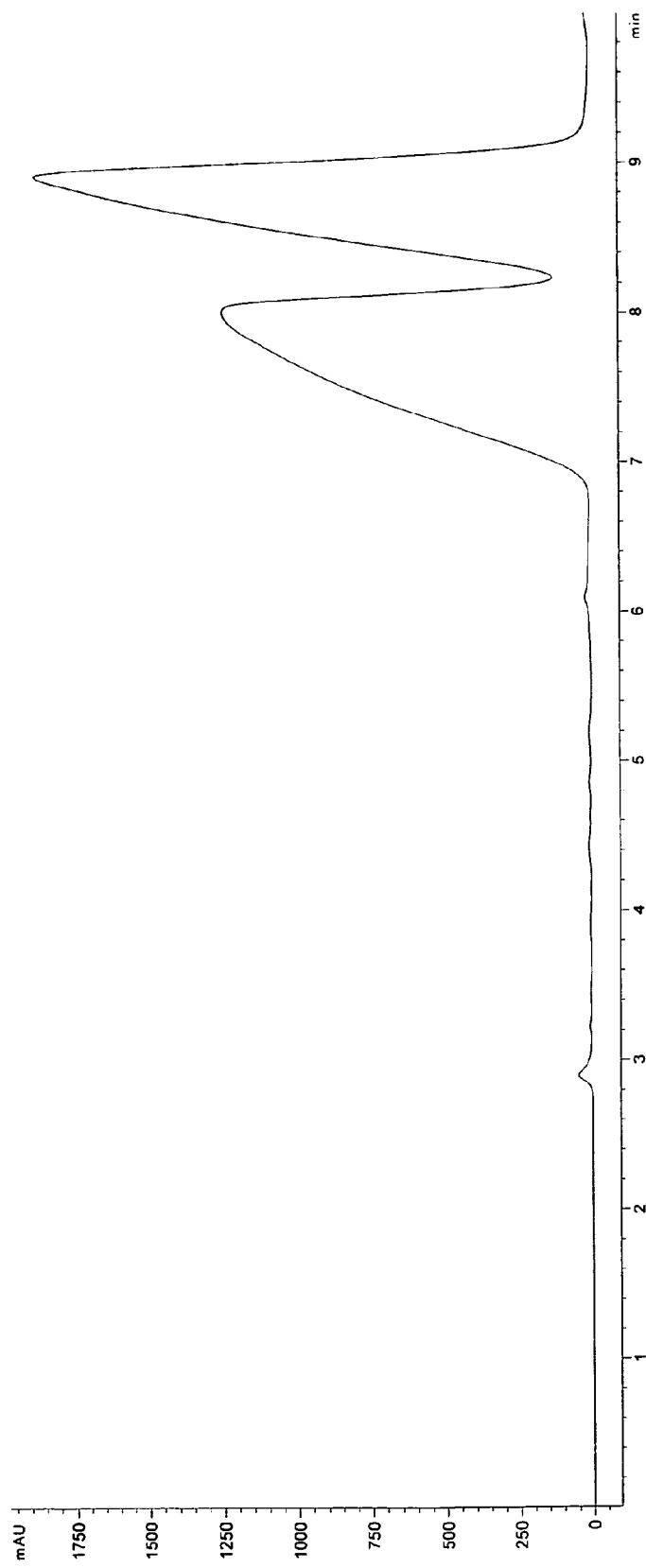
Fig. 16 a) Chromatograms: The influence of the organic acid

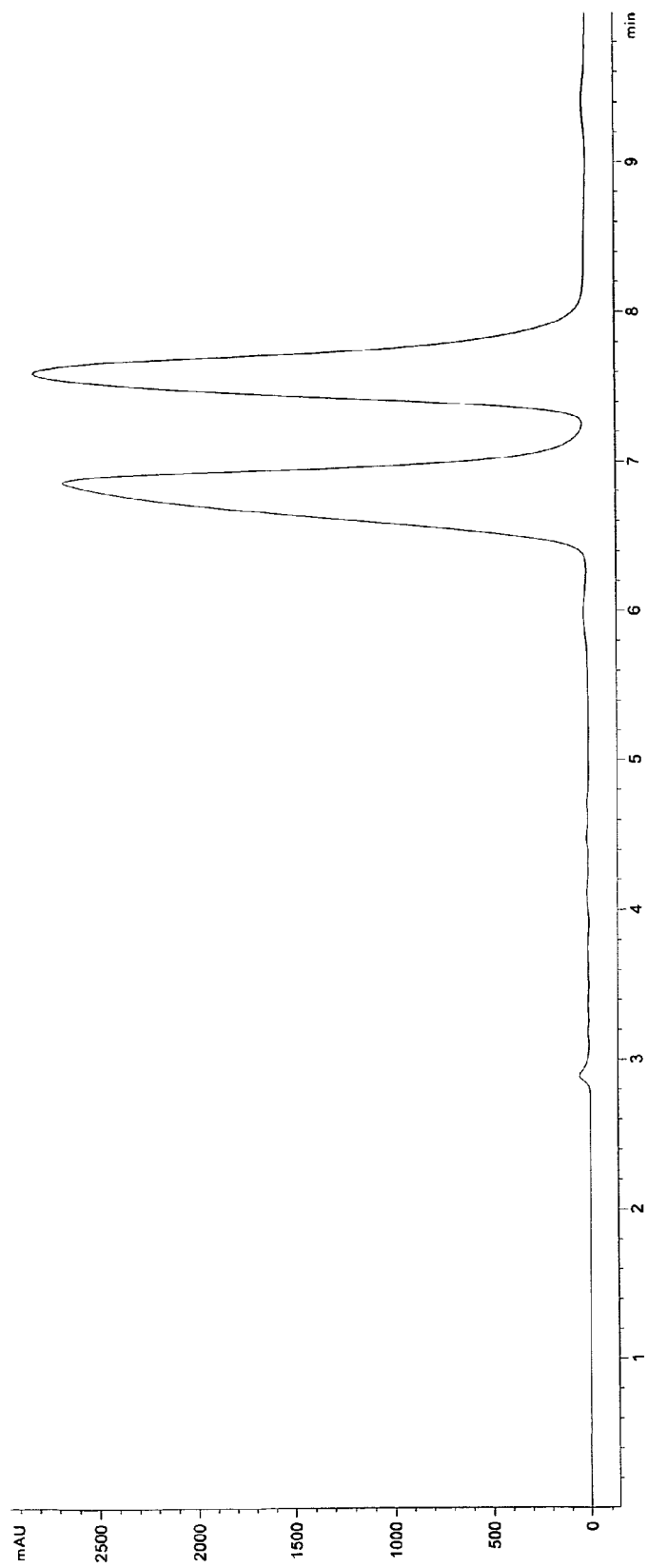
Fig. 16 b) Chromatograms: The influence of the organic acid

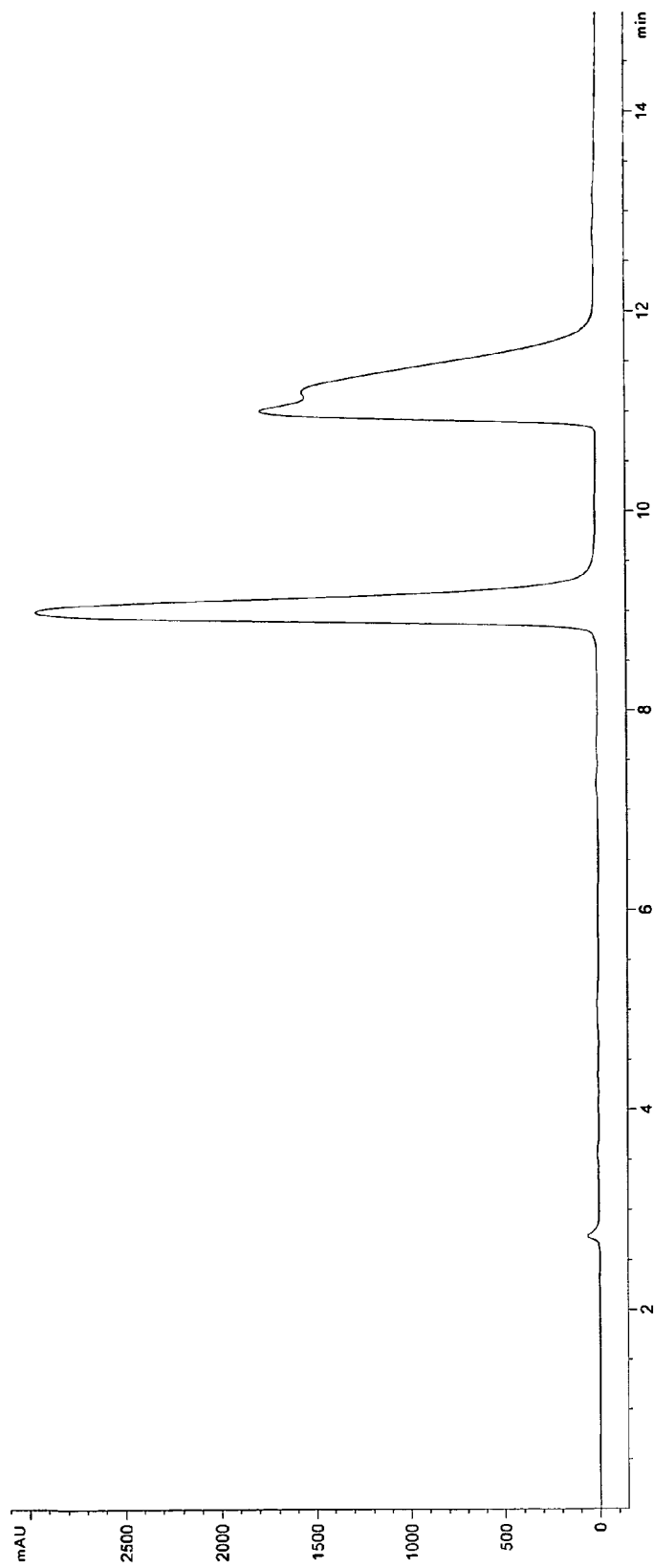
Fig. 16 c) Chromatograms: The influence of the organic acid

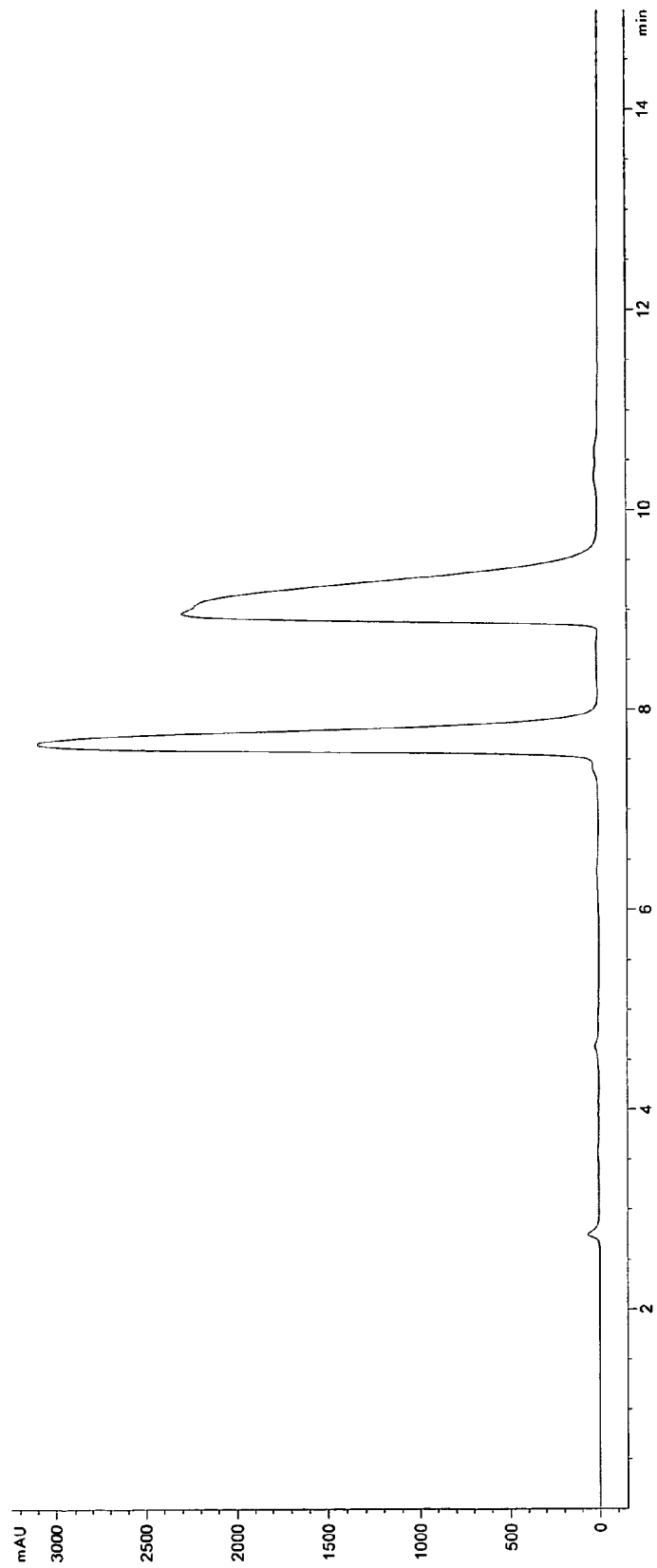
Fig. 16 d) Chromatograms: The influence of the organic acid

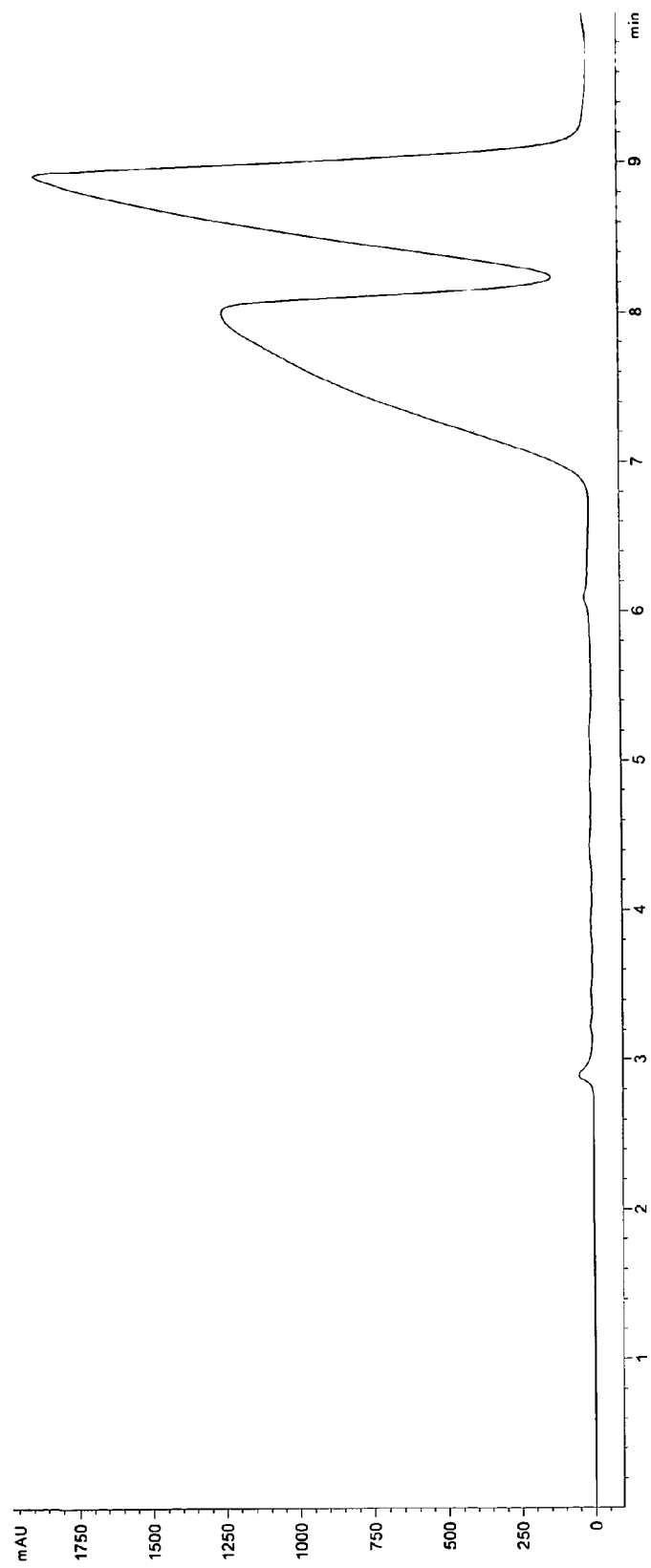
Fig. 17 a) Chromatograms: Loadability

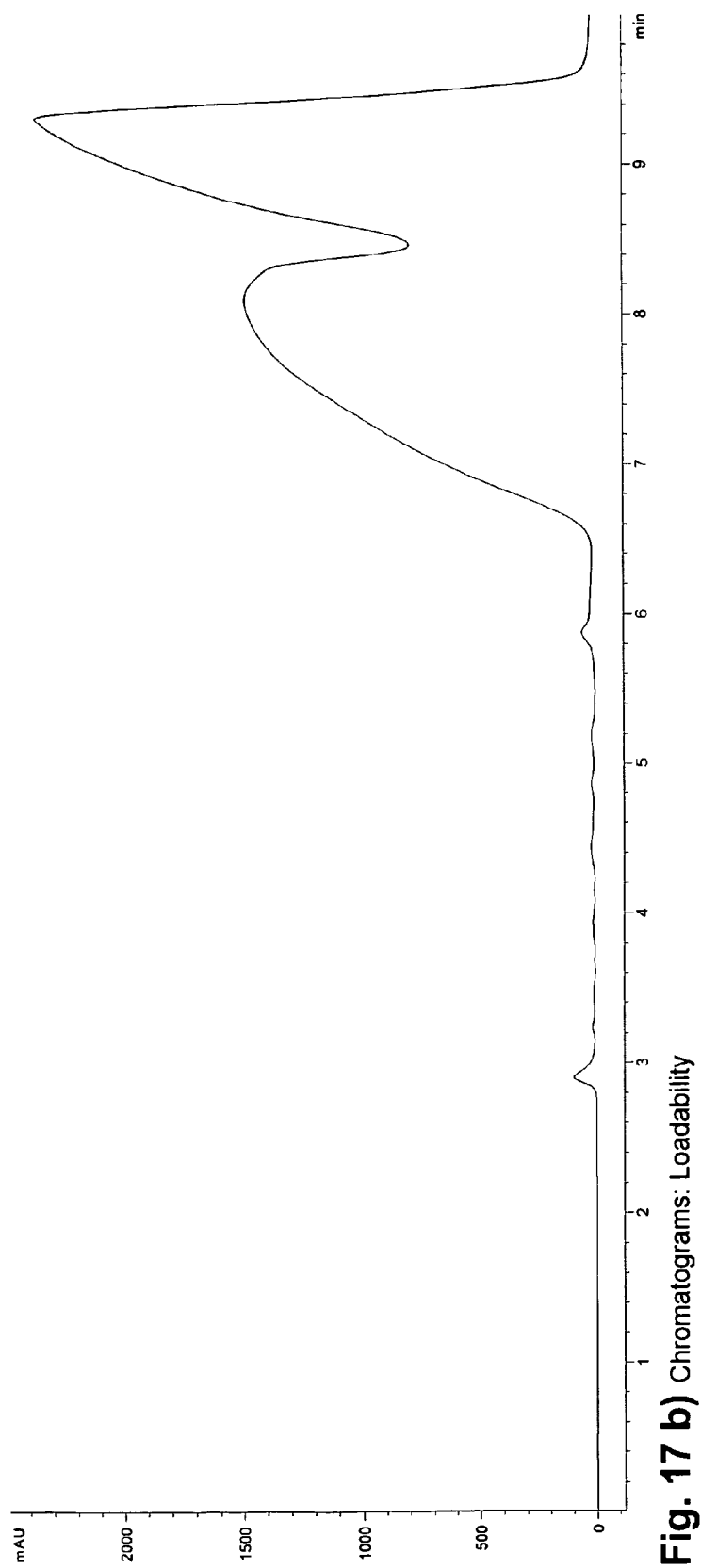
Fig. 17 b) Chromatograms: Loadability

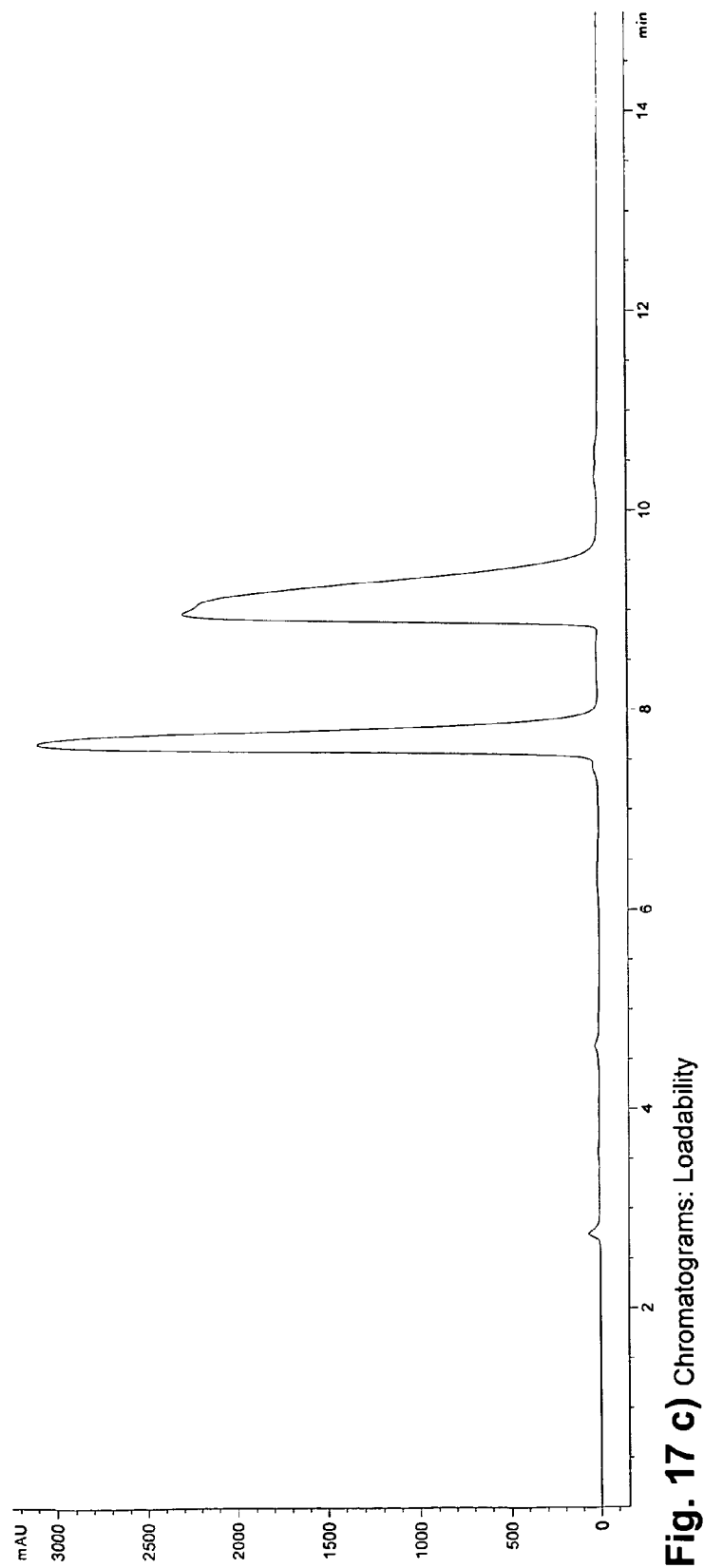
Fig. 17 c) Chromatograms: Loadability

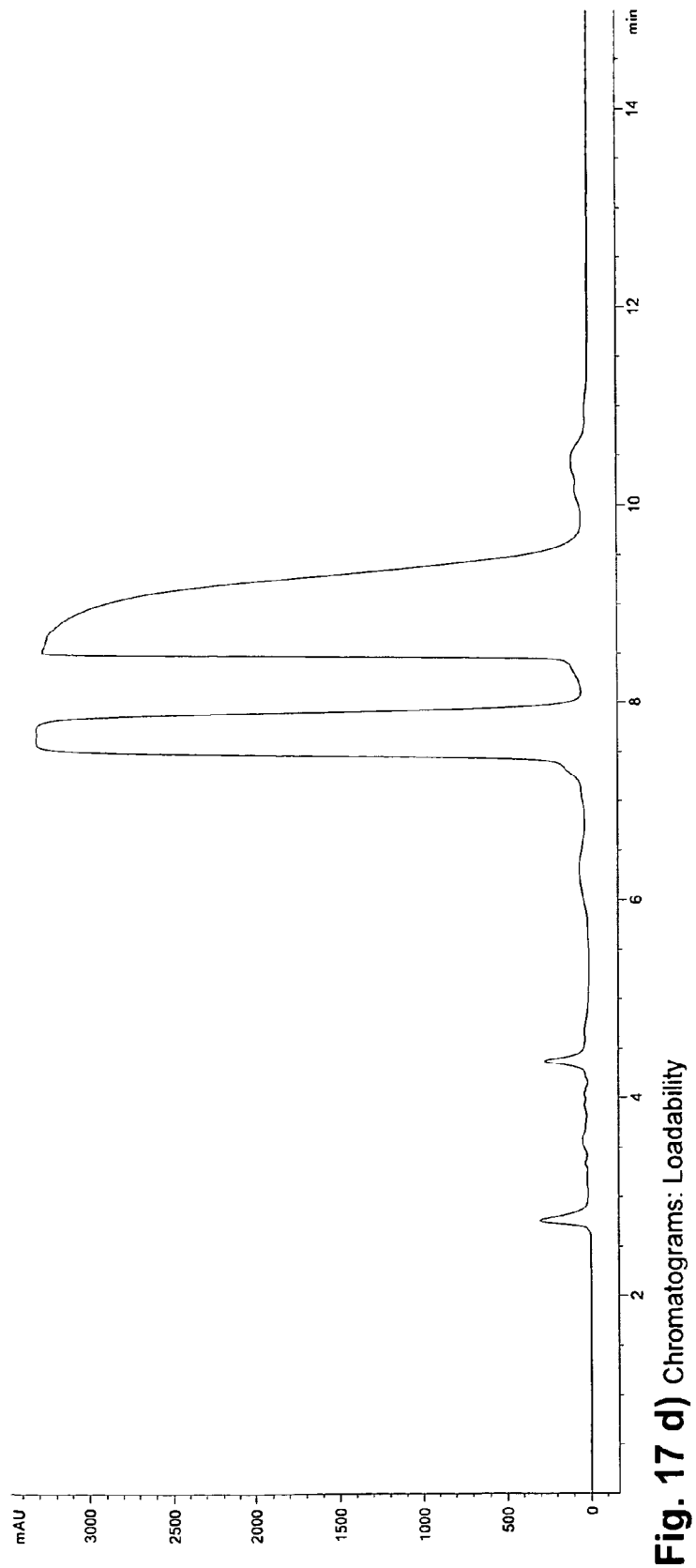
Fig. 17 d) Chromatograms: Loadability

PROCESS OF SEPARATING CHIRAL ISOMERS OF CHROMAN COMPOUNDS AND THEIR DERIVATIVES AND PRECURSORS

This application is the U.S. national phase of International Application No. PCT/EP2012/058415, filed 8 May 2012, which designated the U.S. and claims priority to EP Application No. 11165442.2, filed 10 May 2011, the entire contents of each of which are hereby incorporated by reference.

TECHNICAL FIELD

The present invention relates to the field of separating chiral isomers from each other. Particularly, it relates to the field of separating of chiral isomers of chroman compounds, particularly tocopherols and tocotrienols as well as the esters and intermediates thereof.

BACKGROUND OF THE INVENTION

The presence of chiral centres in a molecule often leads to different chiral isomers. The larger the number of chiral centres in a molecule the larger the number of different isomers is. In the synthesis of such chiral molecules normally a mixture of chiral isomers is formed. However, very often, it is desirable to separate chiral compounds from each other, for example as they have different properties.

Chroman compounds represent an important class of chiral natural products and bioactive compounds. An important class of chroman compounds are vitamin E and its esters. Often vitamin E is commercialized in the form of its esters because the latter show an enhanced stability.

On the one hand the typical technical synthesis of vitamin E leads to mixtures of isomers. On the other hand higher bioactivity (biopotency) has been shown to occur in general by tocopherols and tocotrienols having the R-configuration at the chiral centre situated next to the ether atom in the ring of the molecule (indicated by * in the formulas used later on in the present document) (i.e. 2R-configuration), as compared to the corresponding isomers having S-configuration. Particularly active are the isomers of tocopherols having the natural configuration at all chiral centres, for example (R,R,R)-tocopherols, as has been disclosed for example by H. Weiser et al. in *J. Nutr.* 1996, 126(10), 2539-49. This leads to a strong desire for an efficient process for separating the isomers. Hence, the isomer separation not only of vitamin E, but also of their esters, particularly their acetates, as well as of their precursors is of prime interest.

Chromatographic separation of chiral compounds has been found to be an adequate method for the separation of certain chiral isomers as is disclosed by S. K. Jensen in *Vitamins and Hormones* 2007, Vol. 76, 281-308. Particularly suited for industrial chromatographic separation processes is Simulated Moving Bed (SMB) chromatography as this leads to enhanced separation efficiency and reduced amount of eluent necessary for the separation.

As only a part of the chiral isomers have the desired configuration, any known separation method leads, inherently, only to a small amount of the desired isomer. This amount of a desired isomer gets smaller as the number of chiral centres increases. For explications' sake the following is discussed: if for statistical distribution at each chiral centre is assumed, the amount of the desired isomer is 50% in case of 1 chiral centre, 25% in case of 2 chiral centres, 12.5% in case of 3 chiral centres. As only the desired isomers are the target molecules, the majority of the products synthesized, i.e. the undesired isomers, are typically to be disposed or discarded which is, very costly.

To overcome these inherent problems it has been tried to offer stereospecific synthesis allowing the preferential formation of the desired isomers only. However, these methods are very expensive, complex and/or exotic as compared to the traditional industrial synthesis leading to isomer mixtures.

SUMMARY OF THE INVENTION

Therefore, the problem to be solved by the present invention is to offer a process of separating chiral isomers of chroman compounds, particularly of tocopherols and tocotrienols as well as the esters and intermediates thereof with a higher yield in the desired isomer and which would allow the use of mixtures of isomers being prepared by traditional synthesis processes.

Surprisingly, it has been found the process according to claim 1 is able to solve this problem. This process allows optimizing the yield in principally any of the desired isomers by adjusting the chromatographic separation and isomerization of the non-desired isomers.

As the undesired isomers are isomerized and, hence, partially transformed into desired isomers, the implementation of this process into an industrial production, a method can now be offered which allows almost 100% yield in the desired isomer out of a mixture of isomers without the necessity of employing a stereospecific synthesis route. It has been shown that the present process is easy and can be adapted to the specific need.

It has been, furthermore, found that particularly good separation by a chiral phase is obtained if an eluent is used which consists primarily of a hydrocarbon to which small amounts of an alcohol and/or an organic acid (S1) with a $pK_a$ of less than 6.0 is added.

Further aspects of the invention are subject of further independent claims. Particularly preferred embodiments are subject of dependent claims.

BRIEF DESCRIPTION OF THE DRAWINGS

FIG. 9 shows a schematic representation of a process using multiple separation columns or multiple SMB-units 1 whereby a mixture of isomers of formula (I-A) is separated by columns or multiple SMB-units 1 used in parallel arrangement to yield each of them the desired isomer (I) which is collected and the residual (I') which then is isomerized and re-fed into the stream of isomers of formula (I-A);

FIGS. 10(a) through 10(d) are chromatograms obtained in Example 1 below;

FIGS. 11(a) through 11(d) are chromatograms obtained in Example 2 below;

FIGS. 12(a) through 12(d) are chromatograms obtained in Example 3 below;

FIG. 13 shows the chromatogram of the isomerized product of Example 7;

FIG. 14 shows the chromatogram of the isomerized product of Example 9;

FIGS. 15a) through 15c) show the separation of isomers using different alcohols in the eluent;

FIGS. 16a) through 16d) show the beneficial effect of an organic acid (S1) with a $pK_a$ of less than 6.0 in the eluent; and FIGS. 17a) through 17d) show the beneficial effect of combination of alcohol and organic acid (S1) with a pKa of less than 6.0 in the eluent on the loadability.

DETAILED DESCRIPTION OF THE INVENTION

Figure 1:
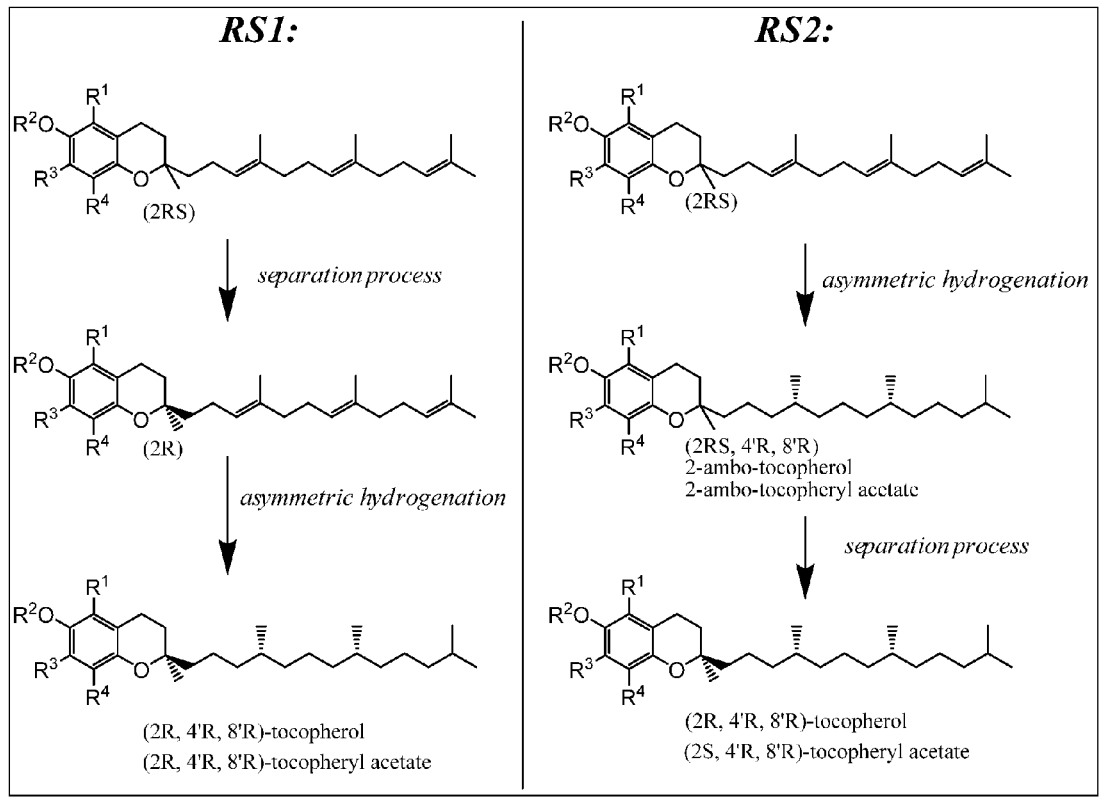
FIG. 1 schematically shows preferred embodiments of producing (2R, 4'R, 8'R)-tocopherol ($R^2$=H)(RS1) and (2R, 4'R, 8'R)-tocopheryl acetate ($R^2$=COCH$_3$)(RS2), respectively.

In a first aspect the present invention relates to a process of separating chiral isomers of formula (I-A) or (I-B) or (I-C)

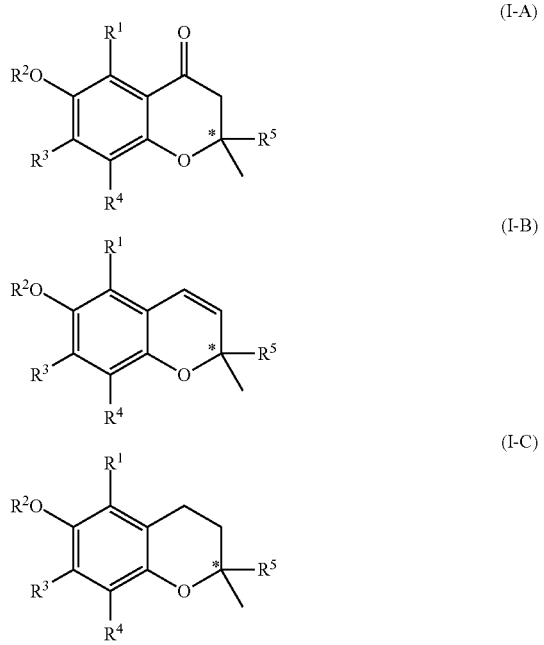

wherein $R^1$, $R^3$ and $R^4$ are independently from each other hydrogen or methyl groups;
$R^2$ represents hydrogen or an phenol protection group;
$R^5$ represents either a linear or branched completely saturated $C_{6-25}$-alkyl group or a linear or branched $C_{8-25}$-alkyl group comprising at least one carbon-carbon double bond;
and wherein * represents the chiral centre of the chiral isomer of formula (I-A) or (I-B) or (I-C);
comprising the steps
a) providing a mixture of at least two isomers of formula (I-A) or (I-B) or (I-C);
b) chromatographic separation of the mixture of isomers of formula (I-A) or (I-B) or (I-C) by means of a chiral phase into desired isomer (I) and residual (I');
c) isomerizing the chirality at the centre indicated by * in formula (I-A) or (I-B) or (I-C) of the isomers of the residual (I') being separated in step b);
d) adding the isomerized isomers obtained in step c) to a mixture of at least two isomers of formula (I-A) or (I-B) or (I-C) being object of further separation;
e) collecting the desired isomer (I).

The term "vitamin E" is used in the present document as a generic descriptor for all tocol and tocotrienol derivatives exhibiting qualitatively the biological activity of α-tocopherol (IUPAC-IUB Recommendation 1981, Eur. J. Biochem. 123, 473-475 (1982)).

The term "(all-rac)-α-tocopherol" identifies (2RS,4'RS, 8'RS)-α-tocopherol, i.e. α-tocopherol having a mixed configuration at all chiral centres (2, 4' and 8').

The term "independently from each other" in this document means, in the context of substituents, moieties, or groups, that identically designated substituents, moieties, or groups can occur simultaneously with a different meaning in the same molecule.

In the present document any dotted line represents the bond by which a substituent is bound to the rest of a molecule.

A "$C_{x-y}$-alkyl", resp. "$C_{x-y}$-acyl" group, is an alkyl resp. an acyl group comprising x to y carbon atoms.

The term "alkyl group" is in the present document to be understood as to be limited not only to strictly, i.e. completely, saturated substituents consisting of C and H, but also to comprise such substituents consisting of C and H having at least one carbon-carbon double bond. Therefore, for example, —$CH_2$—$CH_2$—$CH_2$—$CH_2$—$CH(CH_3)$—$CH_3$ as well as —$CH_2$—$CH$=$CH$—$CH_2$—$CH(CH_3)$—$CH_3$ are considered both to be $C_7$-alkyl groups.

The term "essentially" is used in the present document as to indicate amounts of more than 95%, particularly more than 98%, preferably more than 99%.

The "$pK_a$" is commonly known as negative decadic logarithm of the acid dissociation constant ($pK_a$=−$\log_{10} K_a$). When the organic acid has several protons the $pK_a$ relates to the dissociation of the first proton ($K_{a1}$). The $pK_a$ values indicated are at room temperature. The person skilled in the art knows that the acidities of certain acids are measured in adequate solvents and may vary upon individual measurements or due to the fact the determination of the $pK_a$ has been measured in different solvents and hence different $pK_a$ values can be found for a specific acid. Hence, in a critical case, where for an acid different $pK_a$ values can be found in literature of which at least one is in the $pK_a$ range indicated by the present document—whereas other values are found being outside of said range—it is defined that such an acid is considered to be in the range of $pK_a$ values.

In the present document the term "isomerized" or "isomerization" or "isomerizing" relates to a change in chirality. Therefore, structural isomerization leading to another connectivity of atoms is not meant by this term. Furthermore, for this document, this term also excludes cis/trans isomerization.

The process allows the separation of chiral isomers of formula (I-A) or (I-B) or (I-C). Particularly this separation relates to the separation of chiral isomers having different configuration at the chiral centre(s) but having the same chemical structure, i.e. the same connectivity of atoms.

The residue $R^5$ represents a long chain residue and is particularly responsible for the hydrophobic behaviour of the molecules at issue.

Preferably the group $R^5$ is of formula (II).

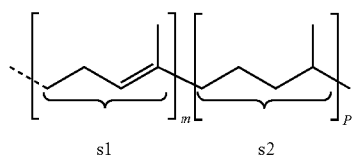
(II)

In formula (II) m and p stand independently from each other for a value of 0 to 5 provided that the sum of m and p is 1 to 5. Furthermore, the substructures in formula (II) represented by s1 and s2 can be in any sequence. The dotted line represents the bond by which the substituent of formula (II) is bound to the rest of formula (I-A) or (I-B) or (I-C).

In one preferred embodiment m stands for 3 and p for 0.

In another preferred embodiment p stands for 3 and m for 0.

In another preferred embodiment are m=1 and p=0. Particularly preferred is cordiachromene (2-methyl-2-(4-methylpent-3-enyl)-2H-chromen-6-ol) which is a known compound exhibiting very specific biological activities, such as anti-inflammatory activity.

Therefore, $R^5$ is preferably of formula (II-A), particularly (II-ARR), or (II-B).

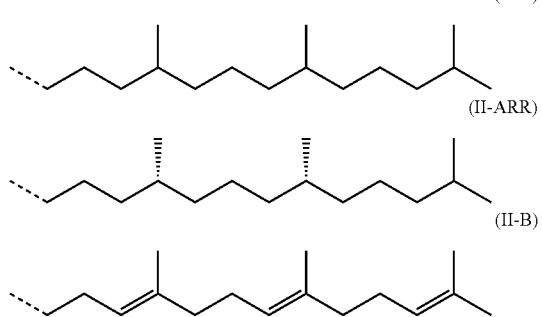

Preferred are the following combinations of $R^1$, $R^3$ and $R^4$:

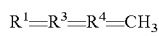
or
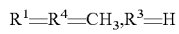
or
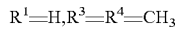
or
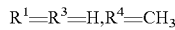

In one embodiment the chiral isomers of formula (I-B) are the isomers of cordiachromene (2-methyl-2-(4-methylpent-3-enyl)-2H-chromen-6-ol).

Most preferably the chiral isomers of formula (I-A) or (I-B) or (I-C) are the isomers selected from the group consisting of α-tocopherol ($R^1=R^3=R^4=CH_3, R^5=$(II-A), particularly (II-ARR), $R^2=H$), β-tocopherol ($R^1=R^4=CH_3, R^3=H, R^5=$(II-A), particularly (II-ARR), $R^2=H$), γ-tocopherol ($R^1=H, R^3=R^4=CH_3, R^5=$(II-A), particularly (II-ARR), $R^2=H$), δ-tocopherol ($R^1=R^3=H, R^4=CH_3, R^5=$(II-A), particularly (II-ARR), $R^2=H$), α-tocotrienol ($R^1=R^3=R^4=CH_3, R^5=$(II-B), $R^2=H$), β-tocotrienol ($R^1=R^4=CH_3, R^3=H, R^5=$(II-B), $R^2=H$), γ-tocotrienol ($R^1=H, R^3=R^4=CH_3, R^5=$(II-B), $R^2=H$), δ-tocotrienol ($R^1=R^3=H, R^4=CH_3, R^5=$(II-B), $R^2=H$), and the esters, particularly the acetates ($R^2=COCH_3$), thereof.

$R^2$ represents either H or a phenol protection group. A protection group is a group which protects the phenolic group ($R^2=H$) and can be deprotected easily, i.e. by state-of-the-art methods, to the phenolic group again.

These two embodiments are structurally strongly related as they can be converted easily to each other by protection resp. deprotection reaction.

Particularly the phenol protection group forms with the rest of the molecule a chemical functionality which is selected from the group consisting of ester, ether or acetal.

In case where the phenol protection group forms with the rest of the molecule an ester, the ester is an ester of an organic or inorganic acid.

If the ester is an ester of an organic acid, the organic acid can be a monocarboxylic acid or a polycarboxylic acid, i.e. an acid having two or more COOH— groups. Polycarboxylic acids are preferably malonic acid, succinic acid, glutaric acid, adipic acid, maleic acid or fumaric acid.

Preferably the organic acid is a monocarboxylic acid.

Hence, the substituent $R^2$ is preferably an acyl group. The acyl group is particularly a linear or branched $C_{1-10}$-alkyl or cycloalkyl or aralkyl group. Preferably the substituent $R^2$ is a benzyl group or a substituted benzyl group, particularly preferred a benzyl group.

The protection group can be easily deprotected by hydrogenation.

If the ester is an ester of an inorganic acid, the inorganic acid is preferably nitric acid or a polyprotic acid, i.e. an acid able to donate more than one proton per acid molecule, particularly selected from the group consisting of phosphoric acid, pyrophosphoric acid, phosphorous acid, sulphuric acid and sulphurous acid.

It is preferred that the protection group is a benzoyl group or a $C_{1-4}$-acyl group, particularly acetyl group. The molecules in which $R^2$ represents an acyl group, particularly an acetyl group, can be easily prepared from the corresponding phenolic ($R^2=H$) compound by esterification, respectively the phenolic compound can be obtained from the corresponding ester by ester hydrolysis. Those reactions and their reaction conditions are well known to the person skilled in the art. It is already known that due to their significantly higher stability, tocopheryl esters, particularly tocopheryl acetate, are used commonly as vitamin E supplements. The tocopheryl esters are readily hydrolysed, for example in the body, to the corresponding free tocopherol.

In case where the phenol protection group forms with the rest of the molecule an acetal, the substituent $R^2$ is preferably

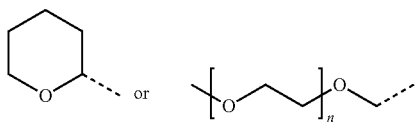

with n=0 or 1.

Hence, the acetals formed so are preferably methoxymethyl ether (MOM-ether), β-methoxyethoxymethyl ether (MEM-ether) or tetrahydropyranyl ether (THP-ether). The protection group can be easily deprotected by acid.

The isomers of formula (I-A) or (I-B) or (I-C) having $R^2$=H can be reacted with a protecting agent to yield isomers of formula (I-A) or (I-B) or (I-C) having $R^2$=phenol protecting group.

The protecting agents leading to the corresponding phenol protection groups are known to the person skilled in the art, as well as the chemical process and conditions for this reaction. If, for example, the phenol protection group forms with the rest of the molecule an ester, the suitable protecting agent is for example an acid, an anhydride or an acyl halide.

In the case that an ester is formed by the reaction of the isomers of formula (I-A) or (I-B) or (I-C) having $R^2$=H with a protecting agent, and that said ester is an ester of an organic polycarboxylic acid or an inorganic polyprotic acid, not necessarily all acid groups are esterified. Preferable esters of inorganic polyprotic acids, are tocopheryl phosphates and ditocopheryl phosphates, particularly α-tocopheryl phosphate and α-ditocopheryl phosphate.

In a preferred embodiment $R^2$ is H.

Particularly, the desired chiral isomers of formula (I-A) or (I-B) or (I-C) are the isomers of a tocotrienol, particularly (2R)-tocotrienol, preferably (2R)-α-tocotrienol, or the acetate thereof.

It has been observed that the isomers having the natural configuration at the chiral centre marked by * are particularly physiologically active. In a lot of cases it is particularly the R-configuration the physiologically particularly active.

This is for example shown by S. K. Jensen in *Vitamins and Hormones* 2007, Vol. 76, 281-308, the entire content of which is hereby incorporated by reference.

Hence, it is preferred that the desired chiral isomers of formula (I-A) or (I-B) or (I-C) has the R-configuration at the carbon marked by * in formula (I-A) or (I-B) or (I-C).

Due to the residue $R^5$ the isomers of formula (I-A) or (I-B) or (I-C) may have other chiral centres. Particularly in one of the preferred embodiments where the isomers comprise the residue $R^5$ of formula (II-A) there exist further chiral centres.

It has been found that particularly the R-configurations at such additional chiral centres in the side chain $R^5$ are physiologically particularly advantageous.

In the most preferred embodiment the desired chiral isomers of formula (I-A) or (I-B) or (I-C) are the isomers (2R, 4'R,8'R)-α-tocopherol or (2R,4'R, 8'R)-α-tocopheryl acetate.

Synthesis of Chiral Isomers of Formula (I-A) or (I-B) or (I-C)

The chiral isomers of formula (I-A) or (I-B) or (I-C) are structurally inter-related and can be transformed easily to each other. The molecules of formula (I-B) may be obtained from molecules of formula (I-A) by reduction to the corresponding alcohols, followed by elimination of water. The molecules of formula (I-C) may be obtained from molecules of formula (I-B) by reduction, e.g. by catalytic hydrogenation.

A preferred way of synthesizing compounds of formula (I-A) is from the corresponding 2-acetyl-methylhydrochinone, 2-acetyl-dimethylhydrochinone resp. 2-acetyl-trimethylhydoquinone of formula (III-A) and the methylketone of formula (IV-A), particularly from farnesylacetone or tetrahydrogeranylacetone in the presence of a base, particular in the presence of pyrrolidine, as disclosed in detail by Kabbe and Heitzer, *Synthesis* 1978; (12): 888-889 the whole disclosure of which is incorporated herein by reference. The phenol protecting group can be introduced by reacting compound of formula (I-A) having $R^2$ being H with a corresponding protecting agent. Kabbe and Heitzer disclose the introduction of an acetyl group by its reaction with acetanhydride in the presence of pyridine and toluene.

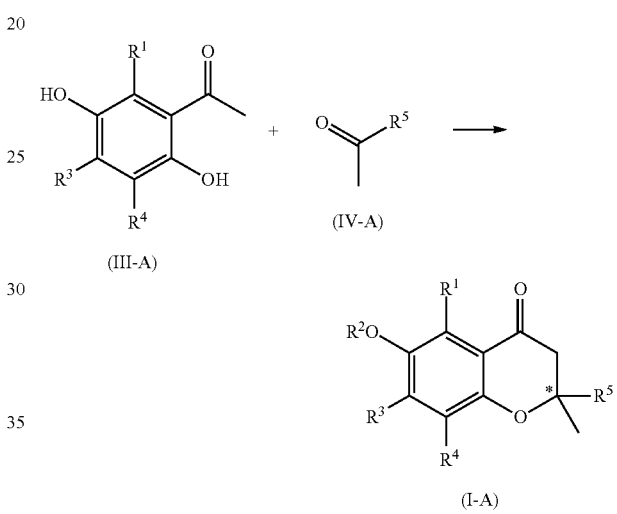

The compound of formula (I-B) can be obtained for example by reduction of formula (I-A) by sodium boranate as disclosed by Kabbe and Heitzer, *Synthesis* 1978; (12): 888-889.

The compound of formula (I-C) can be obtained from chemical transformation of compound of formula (I-B) by reduction, e.g. by partial hydrogenation, particularly by sodium/ethanol such as described in Manecke and Bourwieg, *Chem. Ber.* 95, 1413 (1962) the whole disclosure of which is incorporated herein by reference.

The compound of formula (I-C) can also be obtained from chemical transformation of compound of formula (I-A). Particularly this chemical transformation is made by the reaction of metallic zink in the presence of an acid or an acid mixture, for example as disclosed for in U.S. Pat. No. 6,096,907 the whole disclosure of which is incorporated herein by reference.

The compound of formula (I-C) having a completely saturated $C_{6-25}$-alkyl group as substituent $R^5$ may also be synthesized from the corresponding methyl-, dimethyl-resp. trimethylhydoquinone of formula (III-C) and the corresponding alcohol of formula (IV-C1) resp. (IV-C2) in a known manner (Ullmann's Encyclopedia of Industrial Chemistry, Release 2010, 7th Edition, "Vitamins", page 44-46)

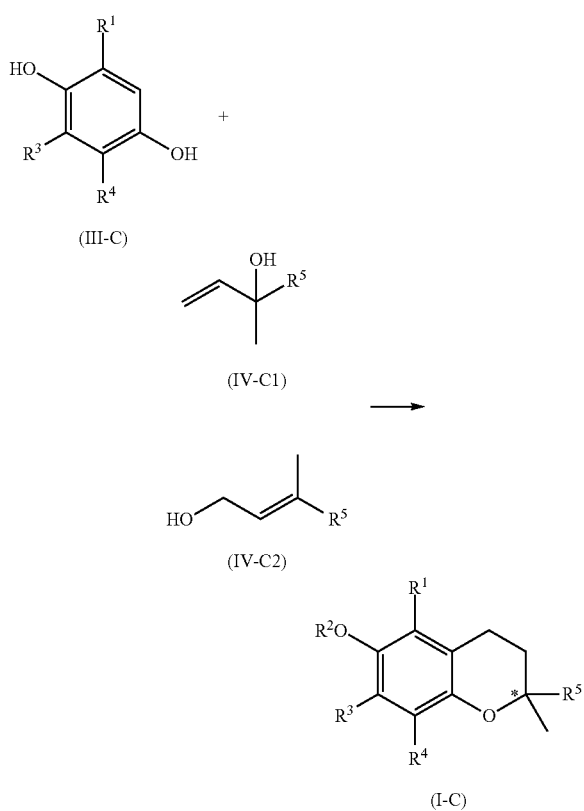

Said reactions are not stereospecific or stereospecific and hence a mixture of isomers of formula (I-C) of R- and S-configuration at the chiral centre marked by * is formed. Typically racemic mixtures of about 50% S- and 50% R-isomers are formed.

If the residue $R^5$ comprises at least one chiral carbon centre the corresponding alcohols of formula (IV-C1) resp. (IV-C2) are typically also mixtures of isomers having different configuration(s) at said additional chiral carbon centre(s). Traditional industrial synthesis yields mixtures of the individual isomers.

For example, in case of $R^5$ being a residue of formula (II-A), the alcohol of formula (IV-C1), resp. (IV-C2), used is isophytol, resp. phytol, which is typically an isomeric mixture of 4 isomers ((R,R)- (R,S)-, (S,R)- and (S,S)-isomer) being synthesized according the traditional methods.

In contrast to this, natural phytol consists only of the R,R-isomer and hence, is isomerically pure.

Therefore, in one preferred embodiment the compound of formula (I-C) is prepared from natural phytol. However, as natural phytol, resp. isophytol, is commercially available only in rather small amounts and is rather expensive, the potential of using natural phytol, resp. isophytol, for industrial scale synthesis of tocopherols is rather limited.

However, new developments enable synthesizing phytol in a preferential formation of a single isomer. For example WO 2006/066863 A1, the entire content of which is hereby incorporated by reference, discloses a method of asymmetrical hydrogenation of alkenes using chiral iridium complexes. It has been found that using this method leads to the desired isomer of the chiral hydrogenation products of the corresponding alkene in selectivity which then can be converted chemically to the desired isomer of phytol resp. isophytol. Phytol respectively isophytol then can be transformed by further known chemical transformations finally to the desired isomer of tocopherol.

Therefore, in another preferred embodiment the compound of formula (I-C) is prepared from isophytol being obtained in a multistep reaction comprising an asymmetrical hydrogenation of alkene in the presence of a chiral iridium complex.

A further possibility of synthesizing tocopherols or their esters, particularly their acetates, i.e. molecule of formula (I-C) having $R^5$ being of formula (II-ARR), is from tocotrienols or their esters, particularly their acetates, i.e. molecule of formula (I-C) having $R^5$ being of formula (II-B), by the above asymmetrical hydrogenation of alkenes using chiral iridium complexes.

FIG. 1 schematically shows the preferred embodiments of producing (2R,4'R,8'R)-tocopherol ($R^2$=H), resp. (2R,4'R, 8'R)-tocopheryl acetate ($R^2$=COCH$_3$).

In the first embodiment, shown by reaction scheme RS1 in FIG. 1, the tocotrienols or their acetates, are first separated (using the separation process according to the present invention) into the isomer having the R-resp. the S-configuration at the chiral atom indicated by * followed by the asymmetrical hydrogenation of the R isomer using chiral iridium complexes.

In the other embodiment, shown by reaction scheme RS2 in FIG. 1, the tocotrienols or their acetates first are asymmetrically hydrogenated using chiral iridium complexes leading to a mixture of (2R,4'R,8'R)-tocopherol and (2S,4'R,8'R)-tocopherol, also known as 2-ambo-tocopherol, resp. their acetates, which then are separated in a further step using the separation process according to the present invention yielding the desired isomer.

In both embodiments the chiral iridium complexes as well as the method of asymmetrical hydrogenation of alkenes using chiral iridium complexes is preferably the one which is disclosed in WO 2006/066863 A1, the entire content of which is hereby incorporated by reference.

The process of separating chiral isomers of formula (I-A) or (I-B) or (I-C) comprising in a first step
a) providing a mixture of at least two isomers of formula (I-A) or (I-B) or (I-C).

The term "mixture of at least two isomers of formula (I-A) or (I-B) or (I-C)" in step a) relates primarily to a mixture of isomers of the same formula having different chirality at the carbon atom indicated by *, i.e. such mixtures are mixtures of R- and S-configuration of isomers of formula (I-A) in a first instance, of formula (I-B) in a second instance and of formula (I-C) in a third instance.

As discussed already above the compound of formula (I-A) and (I-B) and (I-C) are structurally interrelated and can be transferred to each other.

Figure 2:
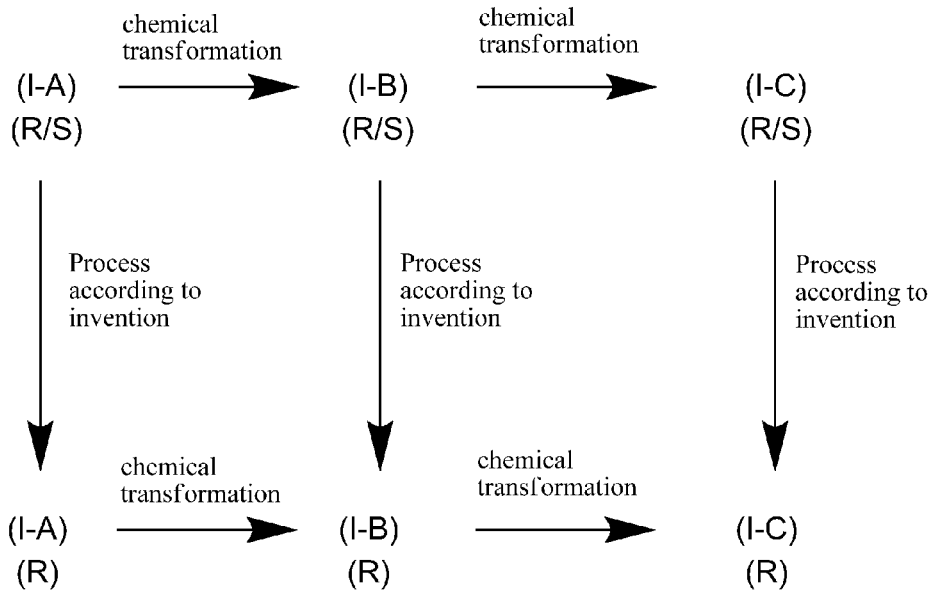
FIG. 2 shows schematically the different possibilities whereby mixtures of R- and S-isomers of formula (I-A) can be chemically transformed to R- and S-isomers of formula (I-B) and whereby mixtures of R- and S-isomers of formula (I-B) can be chemically transformed to R- and S-isomers of formula (I-C)

FIG. 2 shows schematically the different possibilities. The mixture of R- and S-isomers of formula (I-A) can be chemically transformed to R- and S-isomers of formula (I-B) (horizontal arrows). The mixture of R- and S-isomers of formula (I-A) can also be separated into the desired (in the present representation the R-isomer) isomer of formula (I-A) by the process of the present invention (vertical arrow).

Analogously, the desired isomers of formula (I-B), respectively (I-C) may be obtained as it is represented in the scheme of FIG. 2.

Of course the mixtures of isomers of formula (I-B) and (I-C) can be obtained also differently, i.e. not from formula (I-A), resp. (I-B). For example isomers of formula (I-C) can be obtained by the method described before when discussing the synthesis using the alcohol of formula (IV-C1) resp. (IV-C2).

If the side chain, i.e. the substituent $R^5$, has further chiral carbon centres, there might exist more than two isomers in the above mixture.

Chromatographic Separation

The process of separating chiral isomers of formula (I-A) or (I-B) or (I-C) comprises a further step b) chromatographic separation of the mixture of isomers of formula (I-A) or (I-B) or (I-C) by means of a chiral phase into desired isomer (I) and residual (I').

Chromatography is a known separation technique since a long time. It is also known that chiral compounds can be separated by means of using chiral phases.

For the present invention, the chiral phase is a chiral stationary phase (CSP). The chiral stationary phase can be prepared by attaching a suitable chiral compound to the surface of an achiral solid support such as silica gel. The chiral compound may be immobilized or form a coating on the support material. The chiral compound can be adsorbed or chemically bound to the support. Preferably the chiral compound is chemically bound to the support.

Such chiral phases are described in EP 0 157 365 A2, EP 0 155 637 A2, U.S. Pat. Nos. 7,772,153 B2, 4,619,970 and 4,861,872, the entire content of which is hereby incorporated by reference.

It is also possible in certain circumstances that the chiral compound can be used directly as such in the chiral separation. This is particular the case if the chiral compound is of mineral origin or if a highly molecular insoluble chiral polymer is used where no support material is needed.

Preferably, the chiral phase is a polysaccharide or a derivative thereof, particularly immobilized on an achiral solid support such as silica gel. Polysaccharides or derivatives thereof are described for example in *Pure Appl. Chem., Vol.* 79, No. 9, 2007, 1561-1573, the entire content of which is hereby incorporated by reference, as suitable chiral phases.

Particularly suitable chiral phases are those of the group consisting of celluloses, amyloses, chitins, chitosans, xylans, curdlans, dextrans, inulins and cyclodextrines and their derivatives.

Furthermore, in certain cases chiral phases selected from tartrate phases, polyacrylamide phases, chiral coordination complex phases or Charge—Transfer Phases, chiral ion-exchange phases or Pirkle phases may be used for the purpose of the invention.

Particularly preferred chiral phases are those of the group consisting of celluloses, amyloses, dextrans and cyclodextrines and their derivatives.

Particularly suited are amylose tris(3,5-dimethylphenyl-carbamate), cellulose tris(3,5-dimethylphenylcarbamate), cellulose tris(3,5-dichlorophenyl-carbamate), cellulose tris (4-methylphenylcarbamate) or cellulose tris(4-methyl-benzoat) which are immobilized or coated on silica support. Most preferred chiral phases is amylose tris(3,5-dimethylphenyl-carbamate) which is immobilized or coated on silica support.

Particularly suitable are the chiral phases which are commercially available under the trademarks Eurocel® (from Knauer GmbH, Germany), Regispack® (from Regis Technologies, Inc., USA) Chiralcel® and Chiralpak® (from Daicel Chemical Industries Ltd., Japan), preferably Chiralpak® IA, Chiralpak® IB, Chiralpak® IC and Chiralcel® OD, Chiralcel® OD-I (from Daicel Chemical Industries Ltd., Japan).

The particle size of the chiral phase is in one embodiment smaller than 25 micrometer, particularly between 3 and 25 micrometer, preferably between 5 and 25 micrometer. Particularly preferred in this case, the chromatographic separation is undertaken by HPLC (High Performance Liquid Chromatography). It has been found that by using such small particle sizes a better separation of the isomers (in one chromatographic run) can be achieved, however, that a higher pressure is required. The pressure for this particle size is typically larger than 20 bar.

In another embodiment the particle size of the chiral phase is larger than 25 micrometer, particularly between 50 and 70 micrometer. It has been found that by using such larger particle sizes a lower pressure is required, but that the separation of the isomers (in one chromatographic run), however, is much lower. The pressure to be used for the chromatographic separation is for this particle size preferably between 1 and 18 bar, particularly between 2 and 17 bar, preferably between 5 and 15 bar.

It has been shown that an efficient separation can be preferably achieved if a hydrocarbon solvent is used as eluent. Particular suitable hydrocarbon solvents are aliphatic, cycloaliphatic or aromatic hydrocarbons such as $C_6$-$C_8$-alkane particularly n-octane, n-heptane, n-hexane as well as all the structural isomers thereof; cyclohexane, methylcyclohexane; benzene, ethylbenzene, xylene, and toluene or mixture thereof. Preferably only a single hydrocarbon, particularly hexane or heptane, is used as hydrocarbon solvent as eluent.

It has been found that it is preferential that the chromatographic separation in step b) is in presence of at least one alcohol.

As alcohol particularly suitable are alcohols selected from the group consisting of methanol, ethanol, 1-propanol, 2-propanol, 1-butanol, isobutanol, tert.-butanol, 2-methyl-2-butanol, 3-methyl-2-butanol, 3-methyl-1-butanol, 2-methyl-1-butanol and allylalcohol. Preferably the alcohol is n-propanol or iso-propanol. Most preferred is 1-propanol.

Mixtures of alcohols may also be used.

It is preferred that the alcohol is part of the eluent, particularly present combined with the hydrocarbon solvent.

It has been further found that it is preferential that the chromatographic separation in step b) is in presence of at least an organic acid (S1) with a $pK_a$ of less than 6.0, particularly between 0.5 and 6.0, preferably between 3.0 and 6.0, particularly to acetic acid.

Examples for organic acids having with a $pK_a$ of between 3.0 and 6.0, are particularly citric acid, phthalic acid, terephthalic acid, succinic acid, cinnamic acid, formic acid, lactic acid, acetic acid, ascorbic acid, benzoic acid, butanoic acid, propanoic acid and octanoic acid.

Acids having with a $pK_a$ of less than 6.0 are those mentioned above as well as acids such as sulphonic acids or halogenated acids are trifluoroacetic acid, trichloroacetic acid, p-toluenesulphonic acid, benzenesulfonic acid, dodecylbenzenesulfonic acid, methanesulphonic acid, trifluoromethanesulfonic acid and nonafluorobutanesulphonic acid.

It has been shown that unexpectedly the presence of small amounts of an organic acid (S1) with a $pK_a$ of less than 6, particularly between 3.0 and 6.0, preferably acetic acid, enhances the loadability of the chiral phase. In other words by adding small amounts of organic acid larger quantities of isomers can be separated by a given chiral phase. This finding is very important in view of the cost calculation of equipment for an industrial separation.

It is preferred that the eluent used for the chromatographic separation in step b) comprises 85-100% by weight, particularly 90-98% by weight, of a hydrocarbon, particularly of a $C_6$-$C_8$-alkane;

0-10% by weight, particularly 0.1-5% by weight, of an alcohol, preferably 1-propanol or 2-propanol;

0-5% by weight, particularly 0.1-2% by weight, of an organic acid (S1) with a $pK_a$ of less than 6.0, particularly between 3.0 and 6.0, preferably acetic acid.

Preferably the eluent comprises at least one a hydrocarbon, at least one alcohol and at least one organic acid with a $pK_a$ of less than 6.0, particularly between 3.0 and 6.0.

It has been observed that the above eluent comprising $C_6$-$C_8$-alkane and 1-propanol or 2-propanol as eluent and amylose tris(3,5-dimethylphenylcarbamate) which is immobilized or coated on silica support as chiral phase shows extreme good separation properties.

It has been found that for a particularly good separation Simulated Moving Bed (SMB) chromatography is used for the chiral chromatographic separation. Simulated Moving Bed (SMB) chromatography is a known method for separating racemic mixtures and is disclosed for example in U.S. Pat. No. 5,518,625 and WO 03/051867 A1, the entire contents of which is hereby incorporated by reference.

The separation of the chiral isomers of formula (I-A) or (I-B) or (I-C) into desired isomer (I) and residual (I') by means of chiral phase can be complete or partial.

In one embodiment the separation is essentially complete, preferable complete.

In order to explain the separation and isomerization in more detail reference is made to FIGS. 3 to 9, which illustrate by means of schematic chromatograms, respectively diagrams, more details of these aspects of the invention. For simplicity's sake the peak having the lower retention time ($t_{ret}$) is assumed to have the R-configuration and the peak at the higher retention time ($t_{ret}$) has the S-configuration at the chiral centre indicated by *. Of course, in reality the sequence of R- and S-isomer strongly depends on the system and the column material and needs, therefore to be identified by further measurements or derivatisation methods.

Figure 3:
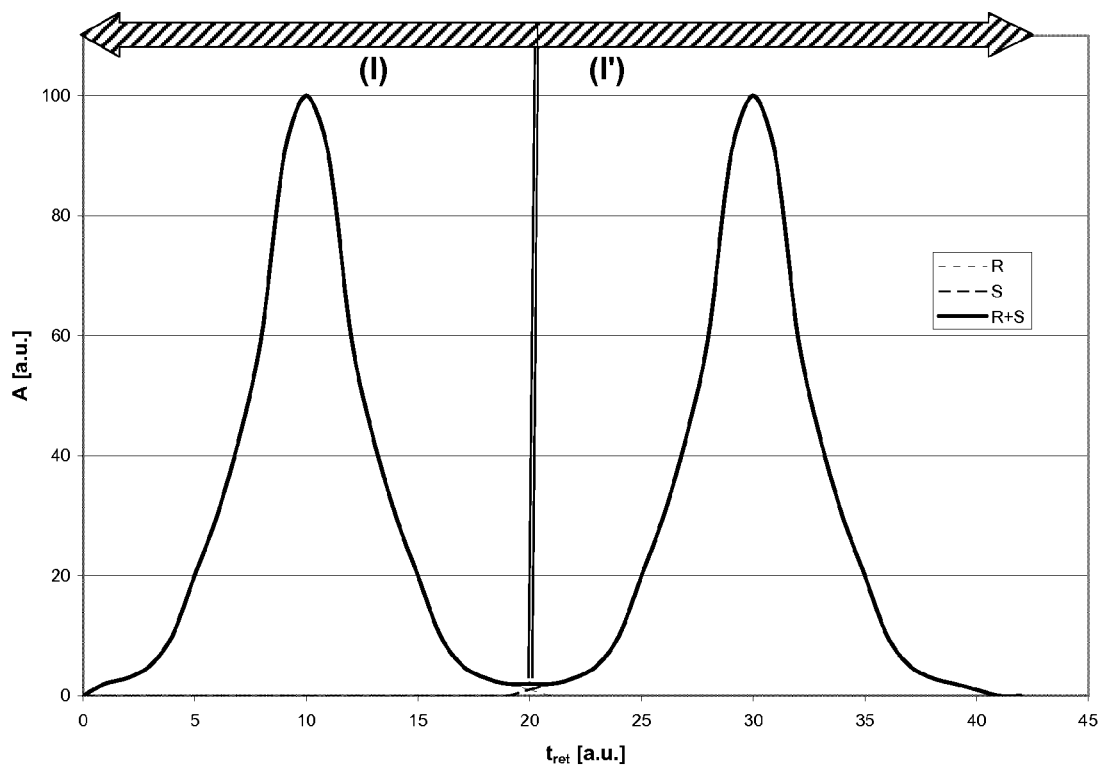
FIG. 3 shows in a schematic chromatogram the situation in which the chiral phase separates the desired isomer (I)

FIG. 3 shows in a schematic chromatogram the situation in which the chiral phase separates the desired isomer (I) (in the present representation the R-isomer) completely as the first eluted component. The x-axis of the schematic chromatogram represents the retention time ($t_{ret}$) in arbitrary units (a.u.). The y-axis of the schematic chromatogram represents the absorbance (A) in arbitrary units (a.u.) by which the isomer distribution is detected. If the eluate (continuous line) is collected until a retention time indicated by the double line, the isomer R (dotted line) can be completely separated form the isomer S (dashed line).

Figure 4:
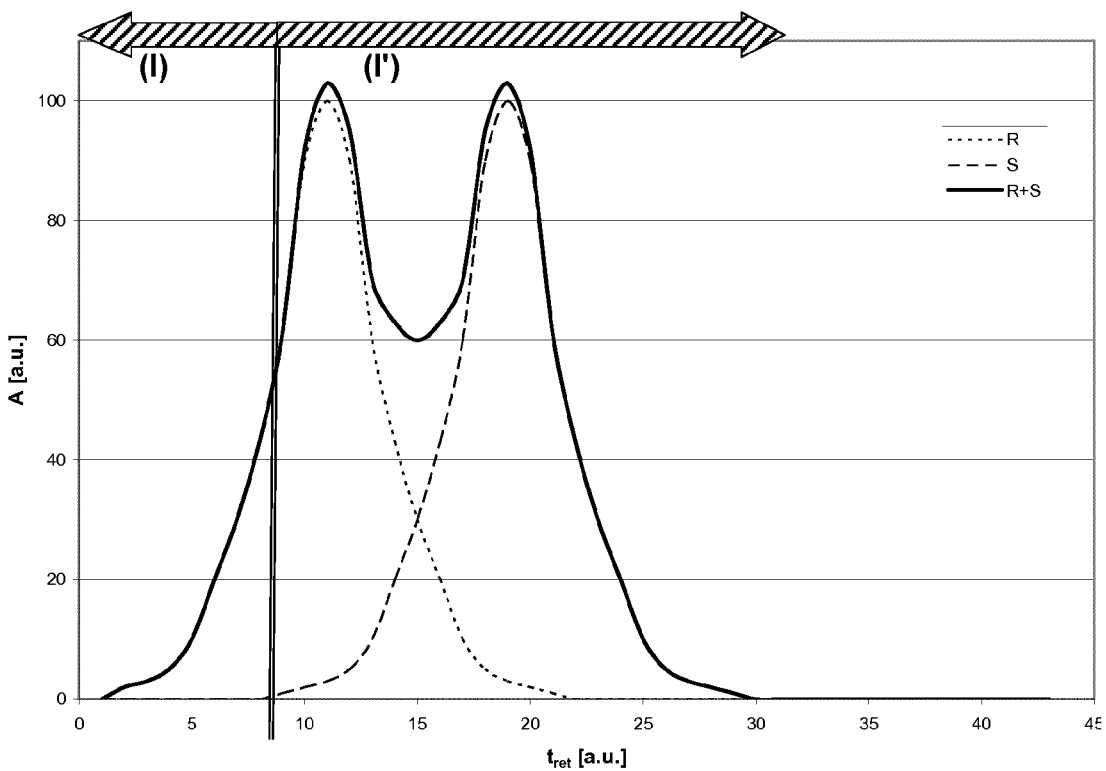
FIG. 4 shows, by means of an analogously schematic chromatogram, the situation in which the chiral phase separates the desired isomer (I)
Figure 5:
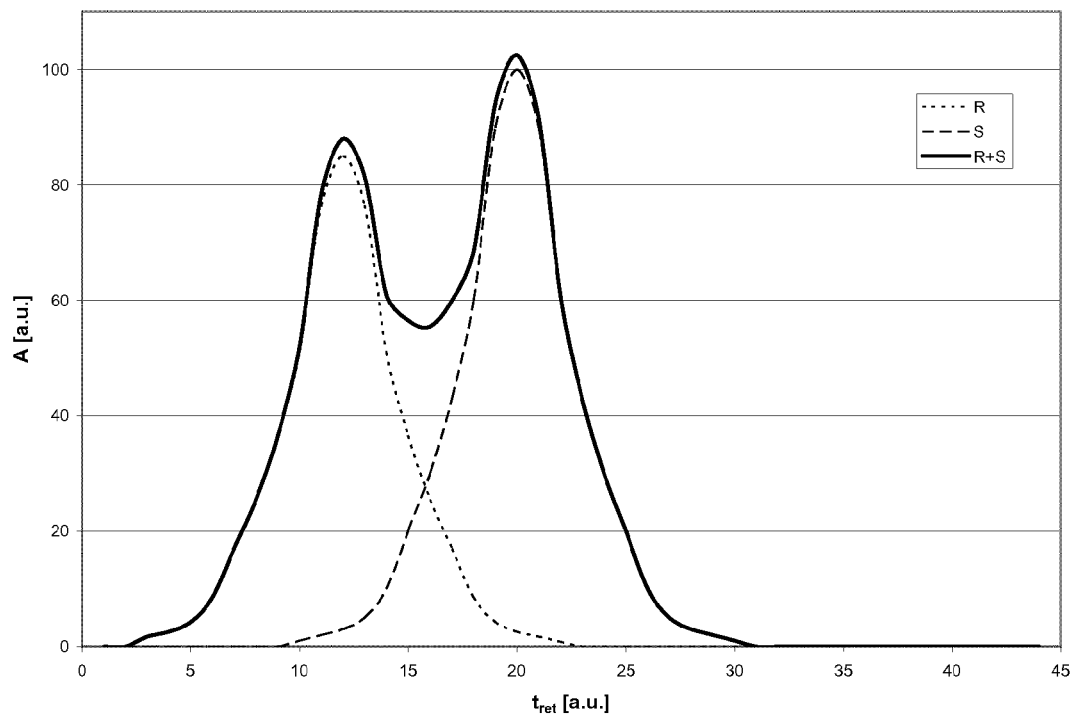
FIG. 5 is a schematic chromatogram of the residual (I') and its isomers R (dotted line) and S (dashed line), respectively.

However, FIG. 4 shows, by means of an analogously schematic chromatogram, the situation in which the chiral phase separates the desired isomer (I) (in the present representation the R-isomer) only partial. If the eluate (continuous line) is collected until a retention time indicated by the double line a part of the desired isomer R (dotted line) may be separated from the residual. The residual in this case comprises not only the isomer S (dashed line) but also some of the desired isomer R. In this schematic example only about 15% of the desired isomer is separated by the separation step b) and the residual (I'), hence, comprises 100% of the S-isomer and about 85% of the desired R-isomer. FIG. 5 shows this situation by a schematic chromatogram of the residual (I') and its isomers R (dotted line) resp. S (dashed line).

It is clear to the person skilled in the art that the previous discussion relates to the case where the R-isomer is the desired isomer. If, however, the S-isomer would be the desired isomer one could separate the S-isomer from the residue by collecting in the schematic chromatogram in FIG. 4 the parts having a retention time of larger than 22 a.u. in said schematic representation and use the part having a retention time up to 22 a.u. as residual which in a following step would than be isomerized.

Isomerization

The process of separating chiral isomers of formula (I-A) or (I-B) or (I-C) comprises a further step c) isomerizing the chirality at the centre indicated by * in formula (I-A) or (I-B) or (I-C) of the isomers of the residual (I') being separated in step b);

The isomerization in step c) may be taken place by different methods.

In one embodiment the isomerization in step c) takes place by exposure of the residual (I') to a temperature of above 150° C., particularly between 160 and 500° C. However the temperatures should not be too high to avoid undesired degradation of the isomers. It has been found that a temperature between 160 and 300° C. give good results. This method of isomerization has been found to be very suitable for the isomerization of isomers of formula (I-B).

In another embodiment the isomerization in step c) takes place by exposure of the residual (I') to a base of which the corresponding acid has a $pK_a$ of larger than 13. The base has suitable basicity to deprotonate an keto-enol proton. Particularly suited as bases are alkoholates of alkali metals, particularly of sodium, potassium and lithium. Preferred bases are bases are sodium methanolate and sodium ethanolate. This method of isomerization has been found to be very suitable for the isomerization of isomers of formula (I-A).

The isomerization can take place batchwise or continuously.

It is preferred that the base being added is removed prior to step d). Preferably the removal is complete.

The base is preferable removed prior to step d), i.e. after the isomerization. This is advantageous in view of the isomerization stability of the final isomers.

In another embodiment the isomerization in step c) takes place by exposure of the residual (I') to an acid of a $pK_a$ of smaller than 2, particularly smaller than 1.

This method of isomerization has been found to be very suitable for the isomerization of isomers of formula (I-C).

On the one hand suitable acids are organic acids, particularly sulphonic acids or halogenated acids, strongly acid ion-exchange resins (particularly containing $SO_3H$ groups), bis (trifluoromethylsulphonyl)imide and methane trisulphonate.

Examples for suitable sulphonic acids or halogenated acids are trifluoroacetic acid, trichloroacetic acid, p-toluenesulphonic acid, benzenesulfonic acid, dodecylbenzenesulfonic acid, methanesulphonic acid, trifluoromethane-sulfonic acid and nonafluorobutanesulphonic acid, or their polymer-bound forms.

On the other hand suitable acids are inorganic acids (mineral acids). Particularly preferred acids are sulfuric acid, hydrochloric acid, phosphomolybdic acid and phosphotungstic acid.

Preferably p-toluenesulphonic acid is used as acid having a $pK_a$ of smaller than 2 for the isomerization in step c).

If case that an acid is used for the isomerization it takes place typically at temperatures of between 50 and 200° C.

It has been found that the isomerization of isomers of formula (I-C) occurs by exposure the residual (I') to an acid of a $pK_a$ of smaller than 2, particularly smaller than 1, at temperatures of higher than 90, particularly at temperatures between 90° C. and 160° C.

The isomerization can take place batchwise or continuously.

It is preferred that the acid having a $pK_a$ of smaller than 2 is added to the residual (I') being separated in step b), particularly in form of an aqueous solution.

In another embodiment the acid having a $pK_a$ of smaller than 2 or the base is immobilized on a solid carrier. In this embodiment the residual (I') being separated in step b) is preferably brought in contact, for example by passing through a column or a packed bed comprising the immobilized acid.

It is preferred that the acid having a $pK_a$ of smaller than 2 being added is removed prior to step d). Preferably the removal is complete. However, small amounts of acids left may be tolerated in certain cases. It is preferred that at least 95% of the acid is removed.

The acid having a $pK_a$ of smaller than 2 is preferable removed prior to step d), i.e. after the isomerization. This is advantageous in view of the isomerization stability of the isomers collected in step e).

The removal may particularly be undertaken by extraction or phase separation.

The isomerization leads to a change of the configuration at the chiral centre indicated by * in formula (I-A) or (I-B) or (I-C). The isomerization in step c) leads to a change of the configuration at the centre indicated by *, so that, after isomerization, the ratio of numbers of molecules in the R-configuration to the one in the S-configuration is about 50:50. It is clear to the person skilled in the art that real isomerization may differ from a ratio of 50:50 despite the isomerization is complete. Although complete isomerization is desired, also incomplete isomerizations are useful for the present invention as long as the amount of desired isomer is increased by the isomerization. It has been found that the ratio of the amount of desired isomer:amount of the non-desired isomer is at least 25:75, particularly at least 30:70, preferably at least 40:60 after the isomerization step.

Figure 6:
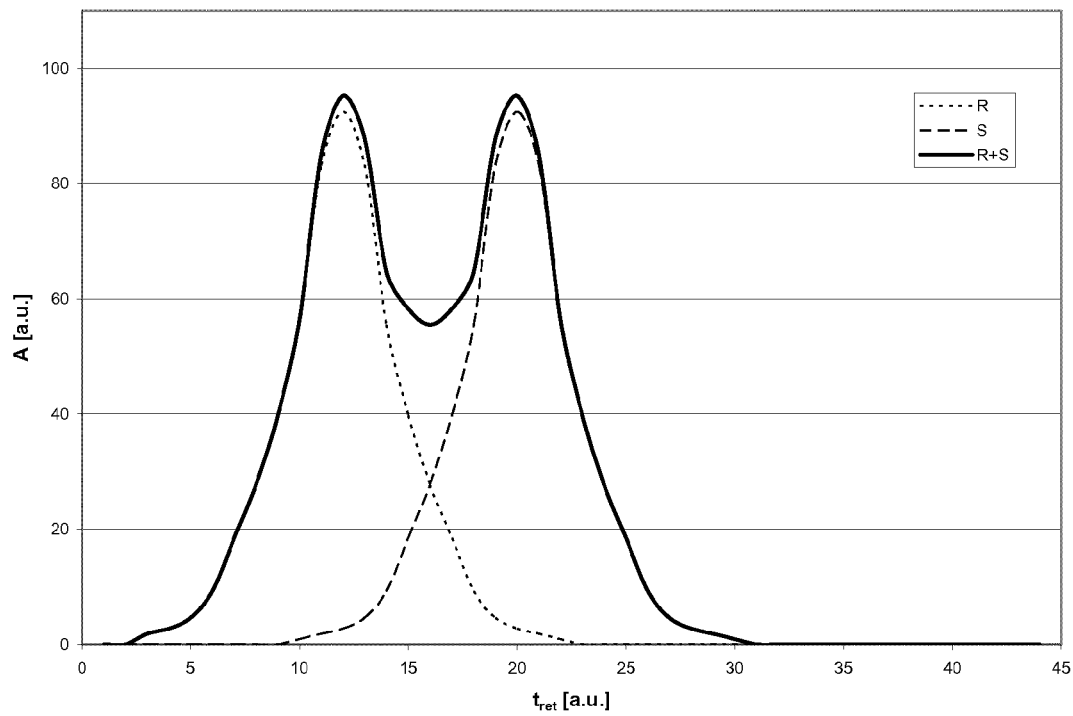
FIG. 6 is a schematic chromatogram showing an optimal situation of a ratio of 50:50 of isomers R (dotted line) and S (dashed line), respectively.

The optimal situation of a ratio of 50:50 is shown by the schematic chromatogram of FIG. 6. As mentioned above for the example of separation of FIG. 4, resp. after separation of the desired isomer (I) for the residual (I') of FIG. 5, the isomerization leads in this example to a schematic chromatogram of FIG. 6 showing the isomerized residual (continuous line) and the individual isomers R (dotted line) respectively isomer S (dashed line).

It is important to realize that the isomerization affects only the chirality of the chiral centres centre indicated by *, but leaves the chirality of other chiral centres, i.e. chiral centres in the side chains, in other words the chiral centres in the residue $R^5$, unchanged.

Remixing

The process of separating chiral isomers of formula (I-A) or (I-B) or (I-C) comprises a further step
 d) adding the isomerized isomers obtained in step c) to a mixture of at least two isomers of formula (I-A) or (I-B) or (I-C) being object of further separation.

Said mixture can be stored and transported or used at once.

Figure 7:
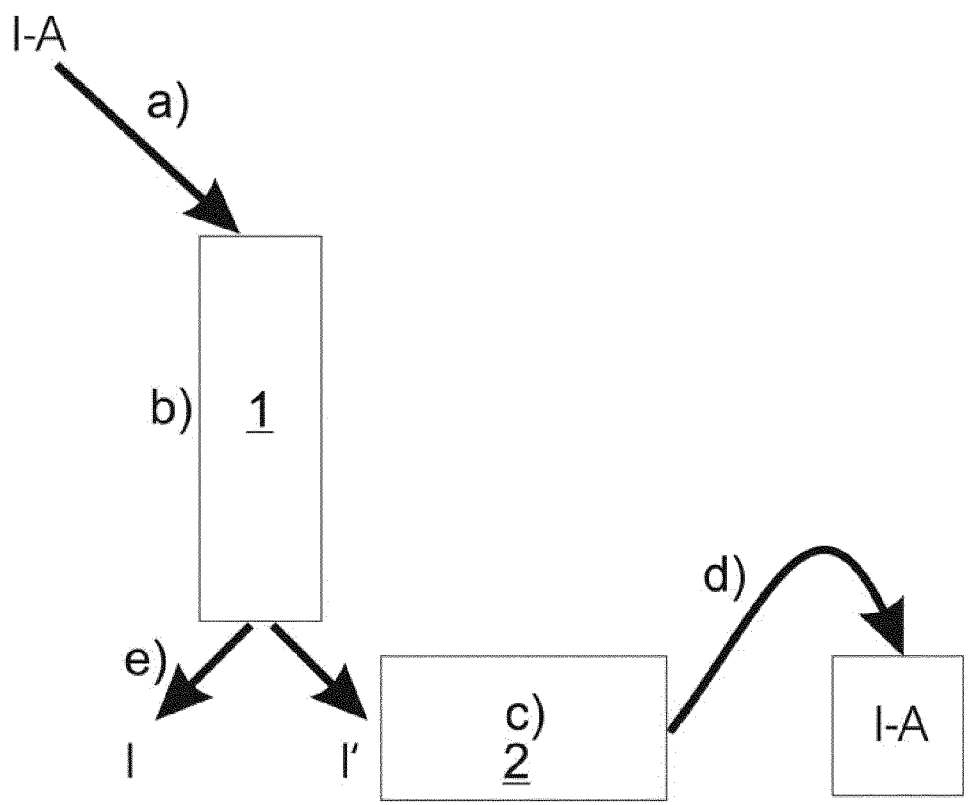
FIG. 7 is a schematic representation for the embodiment in which a mixture of chiral isomers of formula (I-A) is provided in step a); chromatographically separated in step b) by means of a chiral phase 1 into desired isomer (I) and residual (I'); the isomers of the residual (I') are isomerized in step c) and then added to a mixture of isomers of formula (I-A)

FIG. 7 shows a schematic representation for the embodiment in which said mixture is stored. In this representation exemplary a mixture of chiral isomers of formula (I-A) is provided in step a); chromatographically separated in step b) by means of a chiral phase 1 into desired isomer (I) and residual (I'); the isomers of the residual (I') are isomerized in step c) and then added to a mixture of isomers of formula (I-A). This mixture can be stored until a further separation is desired. In the shown representation the isomerization is performed by contacting the residual (I') with a column 2 comprising the immobilized acid. The desired isomer (I) is collected in step e).

It is, however, preferred that the process of the current invention is a continuous process, particularly in that the mixture of at least two isomers of formula (I-A) or (I-B) or (I-C) being object of further separation is the mixture of at least two isomers of formula (I-A) or (I-B) or (I-C) of step a). So in other words it is preferred that the isomerized isomers obtained in step c) are added to a stream of at least two isomers of formula (I-A) or (I-B) or (I-C) in step a).

Figure 8:
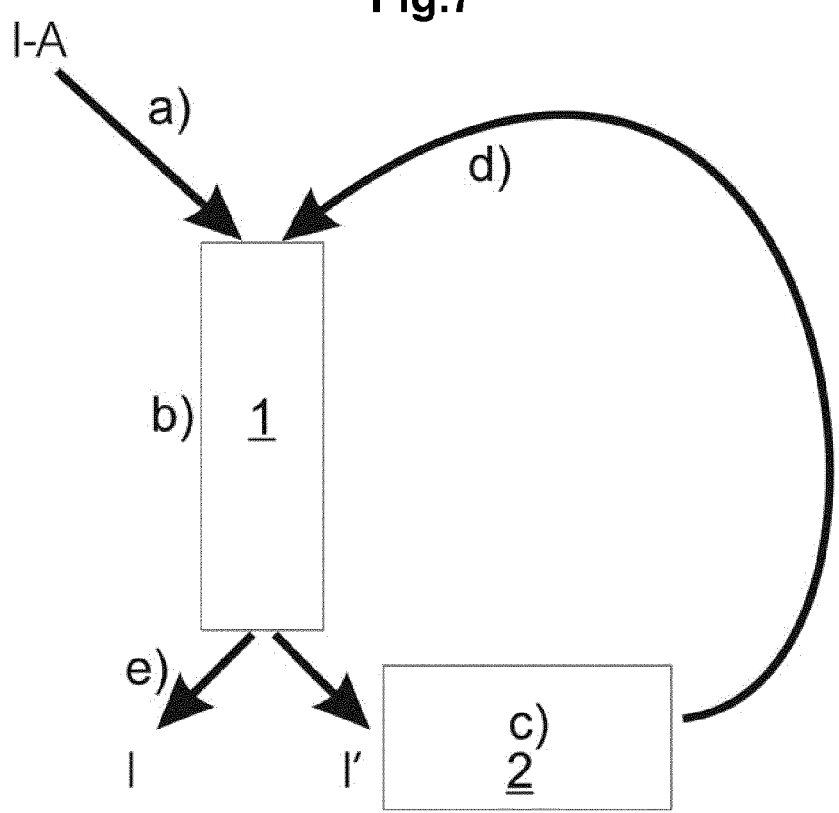
FIG. 8 is a schematic representation of a mixture of chiral isomers of formula (I-A) being provided in step a), chromatographically separated in step b) by means of chiral phase 1 into desired isomer (I) and residual (I'); the isomers of the residual (I') isomerized in step c) and then fed to an incoming stream of mixture of isomers in step a)

This situation is represented schematically in FIG. 8. In this representation exemplary a mixture of chiral isomers of formula (I-A) is provided in step a), chromatographically separated in step b) by means of chiral phase 1 into desired isomer (I) and residual (I'); the isomers of the residual (I') isomerized in step c) and then fed to an incoming stream of mixture of isomers in step a). In the shown representation the isomerization is performed by contacting the residual (I') with a column 2 comprising the immobilized acid.

This process is much preferred as it allows in a very cost efficient way to produce continuously the desired isomer (I) collected in step e), i.e. directly after the separation of desired isomer (I) and residual (I') in step b).

Collecting

The process of separating chiral isomers of formula (I-A) or (I-B) or (I-C) comprises a further step
 e) collecting the desired isomer (I).

The desired isomer (I) is preferably collected directly after chromatographic separation in step b).

Said process produces in an efficient way the desired isomer (I) out of a mixture of at least two isomers of formula (I-A) or (I-B) or (I-C). The process is the more efficient the better the separation of the isomers is in step b).

It has been observed that said separating efficiency is higher if particle sizes of the chiral phase is in one embodiment smaller than 25 micrometer, particularly between 3 and 25 micrometer are used in combination with HPLC, particularly in case that the eluent used for the chromatographic separation in step b) comprises a hydrocarbon and an alcohol and/or an organic acid (S1) with a $pK_a$ of less than 6.0, particularly between 3.0 and 6.0.

However, when high pressure in the chromatography particularly when Simulated Moving Bed (SMB) chromatography is used, there arise high requirements for the equipment allowing a reliable continuous production. Particularly high technical requirements are those for the pumps, valves and joints. These high requirements lead to a remarkable costly expenditure.

As the condition of the present process are leading neither to deterioration nor to remarkable degradation of the compounds of formula (I-A) or (I-B) or (I-C) the number of cycles b)-c)-d) is not very critical. Hence, a lower efficiency in separating the isomers of the isomers (I-A) or (I-B) or (I-C) due to larger particle sizes of the chiral phase, i.e. larger than 25 micrometer, combined with lower pressure is not necessary disadvantageous per se as lower expenditure is necessary in view of equipment and maintenance. Therefore, it may be financially well favourable to operate the separation process on a manifold of low-cost columns or SMB-units operated at low pressure and using several additional cycles rather than using high pressure SMB equipment with columns packed with particles between 3 and 25 micrometer having high separation efficiency.

FIG. 9 shows a schematic representation of a process using multiple separation columns or multiple SMB-units 1. In this representation the mixture of isomers of formula (I-A) is separated by columns or multiple SMB-units 1 used in parallel arrangement to yield each of them the desired isomer (I) which is collected and the residual (I') which then is isomerized and re-fed into the stream of isomers of formula (I-A). The column, resp. SMB-unit 1, shown in separation process is operated at low pressure of typically between 5 and 15 bar and uses chiral phase of particle size of more than 25 micrometer. The separation efficiency is relative low which can be visualized by the schematic chromatogram represented by FIG. 4. In the shown representation the isomerization is performed by contacting the residual (I') with a column 2 comprising the immobilized acid.

The disclosed process enables separating the isomers in industrial scale. In using the process in a continuous way due to the isomerization step almost all undesired isomers can be converted to the desired isomer. Hence, almost no undesired isomers being produced by non-stereospecific synthesis needs to be discarded and, hence, a yield of almost in 100% in the desired isomer can be obtained. This is economically and ecologically particular advantageous and, therefore, represents a remarkable and important step forward in the development in this field of technology.

A further aspect of the invention represents a method of producing a compound of formula (I-C) having a substituent $R^5$ of formula (II-ARR) and the desired configuration, particularly having the R-configuration, at the chiral centre indicated by *.

In this method, in a first step the isomer having the desired, particularly the R-, configuration at the chiral centre indicated by * is collected by using the process—described above in detail—of separating chiral isomers of formula (I-C) having a substituent $R^5$ of formula (II-B). In a second step the desired isomer is then hydrogenated by an asymmetrical hydrogenation using a chiral iridium complex, to yield the compound of formula (I-C) having a substituent $R^5$ of formula (II-ARR) and the desired configuration, particularly having the R-configuration, at the chiral centre indicated by *. The chiral iridium complexes and the asymmetrical hydrogenation are particularly those described in WO 2006/066863 A1.

Hence, in a preferred embodiment, (2R,4'R,8'R)-tocopherols, particularly (2R,4'R,8'R)-α-tocopherol, respectively (2R,4'R,8'R)-tocopheryl acetates, particularly (2R,4'R,8'R)-α-tocopheryl acetate, can be obtained by an asymmetrical hydrogenation using a chiral iridium complex from (2R)-tocotrienol, particularly (2R)-α-tocotrienol, which has been formerly obtained using the above mentioned separation process from tocotrienol, respectively tocotrienyl acetate, particularly from α-tocotrienol, respectively α-tocotrienyl acetate (see also reaction scheme RS1 in FIG. 1).

In a variant of said method, in a first second step the isomers of formula (I-C) having a substituent $R^5$ of formula (II-B) are hydrogenated by an asymmetrical hydrogenation using a chiral iridium complex, to yield the compound of formula (I-C) having a substituent $R^5$ of formula (II-ARR) and the mixture of R/S configuration at the chiral centre indicated by * which in a second step is then separated using the process—described above in detail- to yield compound of formula (I-C) having a substituent $R^5$ of formula (II-ARR) and the desired configuration, particularly having the R-configuration, at the chiral centre indicated by *. The chiral iridium complexes and the asymmetrical hydrogenation are particularly those described in WO 2006/066863 A1.

Hence, a further method of producing (2R,4'R,8'R)-tocopherols, particularly (2R,4'R,8'R)-α-tocopherol, respectively (2R,4'R,8'R)-tocopheryl acetates, particularly (2R,4'R,8'R)-α-tocopheryl acetate, is by the above mentioned separation process from 2-ambo-tocopherol, respectively from 2-ambo-tocopheryl acetate, which has been formerly obtained from tocotrienol, respectively tocotrienyl acetate, particularly from α-tocotrienol, respectively α-tocotrienyl acetate by asymmetrical hydrogenation using a chiral iridium complex (see also reaction scheme RS2 in FIG. 1).

Therefore, in one preferred embodiment the process is such that the desired chiral isomer is tocopherol or tocopheryl acetate obtained from tocotrienol, respectively tocotrienyl acetate, by a step of asymmetrical hydrogenation using a chiral iridium complex which takes place either before step b) or after step e).

In further embodiment of the invention the separating of chiral isomers of formula (I-A) or (I-B) or (I-C) in which $R^2$ represents hydrogen and then reacted in a step f) with the protecting agent to yield the protected chiral isomer of tocopherol of formula (I-A) or (I-B) or (I-C). Hence, the process further comprises a step f) reacting the desired isomer (I) with a protecting agent.

Therefore, preferably (2R,4'R,8'R)-tocopherols, particularly (2R,4'R,8'R)-α-tocopherol, is as described above in detail, separated and collected as desired isomer (I) and reacted in step f) with a protecting agent, to yield (2R,4'R,8'R)-tocopherols, particularly (2R,4'R,8'R)-α-tocopherol, in its protected form, preferably (2R,4'R,8'R)-tocopherols acetate, particularly (2R,4'R,8'R)-α-tocopherol acetate.

The chiral isomers of formula (I-A) or (I-B) or (I-C) being separated by the process of the present invention can be used in several fields of application. Particularly they find use in the field of food or feed or beverage or pharmaceuticals. Particularly in these fields it is very advantageous or is even necessary to offer chiral compounds in a predetermined chirality. Particularly beneficial for these fields of application is if only a single desired isomer out of an initial isomer mixture can be separated. The present process of separation is enabling that target.

In a further aspect the present invention relates, hence, to a food or feed or beverage comprising the desired chiral isomer of formula (I-A) or (I-B) or (I-C) which has been separated by a process of separating chiral isomers of formula (I-A) or (I-B) or (I-C) as described above. Particularly, such food or feed or beverage comprises (2R,4'R,8'R)-tocopherols, particularly (2R,4'R,8'R)-α-tocopherol, or (2R,4'R,8'R)-tocopheryl acetates, particularly (2R,4'R,8'R)-α-tocopheryl acetate.

In a still further aspect the present invention relates, hence, to a pharmaceutical composition comprising the desired chiral isomer of formula (I-A) or (I-B) or (I-C) which has been separated by a process of separating chiral isomers of formula (I-A) or (I-B) or (I-C) as described above. Particularly, such pharmaceutical composition comprises a desired isomer of cordiachromene (2-methyl-2-(4-methylpent-3-enyl)-2H-chromen-6-ol).

LIST OF REFERENCE SIGNS

1 Chiral phase, column, SMB-unit
2 Column comprising the immobilized acid
I desired isomer
I' residual
I-A mixture of chiral isomers of formula (I-A)

EXAMPLES

The present invention is further illustrated by the following experiments.

1. Chromatographic Separation

Starting Materials:
Solvents and reagents used as received were heptane (Fluka, 51750), ethanol (Merck, 1.00983), isopropanol (Sigma-Aldrich, 59300) and acetic acid (Fluka, 45730).

Chromatography:

Preparative separations were performed on an Agilent 1100 series hplc system consisting of an Agilent 1100 degasser, Agilent 1100 preparative pump, Agilent 1100 diode array detector, Agilent 1100 MPS G2250A autosampler/fraction collector controlled by chemstation/CC-mode software package.

HPLC Conditions for Preparative Separation:
Column: Daicel Chiracel® OD-H, 250 mm×20 mm; eluent 0.5% isopropanol, 0.2% acetic acid in n-heptane; flow 13 ml/min; detection 220 nm, 400 µl injection.

Separation of (R)-6-hydroxy-2,5,7,8-tetramethyl-2-((3E,7E)-4,8,12-trimethyl-trideca-3,7,11-trienyl) chroman-4-one and (S)-6-hydroxy-2,5,7,8-tetramethyl-2-(3E,7E)-4,8,12-trimethyltrideca-3,7,11-trienyl) chroman-4-one Example 1

6-Hydroxy-2,5,7,8-tetramethyl-2-((3E,7E)-4,8,12-trimethyltrideca-3,7,11-trienyl) chroman-4-one was prepared according to the example 6a in Kabbe and Heitzer, Synthesis 1978; (12): 888-889.

The product was analyzed by HPLC (Column: Daicel Chiracel® OD-H, 250 mm×4.6 mm; eluent 1% ethanol in n-hexane; flow 1 ml/min; detection 220 nm, 2 µl injection). FIG. 10b) shows this chromatogram. It shows that the product is a 49.5:50.5 mixture (Retention time 13.2 and 14.2 min.)

87.5 mg of this product in heptane was injected and the two peaks with retention time at maximum 35.4 min. (1) (50.9%) resp. 43.5 min. (2) (49.1%) were separated by the preparative HPLC separation. FIG. 10a) shows the chromatogram of the preparative HPLC separation.

After evaporation to dryness and dissolution the two collected fractions have been reanalysis on an analytical column (Daicel Chiracel® OD-H, 250 mm×4.6 mm; eluent 1% ethanol in n-hexane; flow 1 ml/min; detection 220 nm, 2 µl injection). FIG. 10c), respectively FIG. 10d), show the chromatogram of the first fraction, respectively the second fraction. The separation of the two isomers (Retention time 13.2 min, resp. 14.2 min) in the two fraction shows to be 94.9:5.1 (FIG. 10c)) resp. 7.1:92.9 (FIG. 10d)). Hence, the two isomers have been separation by preparative chromatography almost completely.

Separation of (2R)-tocopherols and (2S)-tocopherols

Example 2

Separation of (all-rac)-α-tocopherol (all-rac)-α-tocopherol (DSM Nutritional Products was analyzed by HPLC (Column: Daicel Chiracel® OD-H, 250 mm×4.6 mm; eluent 0.5% ethanol in n-heptane; flow 1 ml/min; detection 220 nm, 2 µl injection). FIG. 11b) shows this chromatogram (Retention time 7.2 resp. 8.2 min, 50:50).

140 mg (all-rac)-α-tocopherol (DSM Nutritional Products) in heptane were injected and two peaks with retention time at maximum of 12.6 min (1) (50.1%) and 14.2 min (2) (49.9%) were separated by the preparative HPLC separation. FIG. 11a) shows the chromatogram of the preparative HPLC separation.

After evaporation to dryness and dissolution the two collected fractions have been reanalysis on an analytical column (Daicel Chiracel® OD-H, 250 mm×4.6 mm; eluent 0.5% ethanol in n-heptane; flow 1 ml/min; detection 220 nm, 2 µl injection). FIG. 11c), respectively FIG. 11d), show the chromatogram of the first fraction (Retention time 7.2 min), respectively the second fraction (Retention time 8.2 min). The separation of the two isomers has been shown to be complete. The isomers have been identified to be (2R)-α-tocopherol (FIGS. 11c) and (2S)-α-tocopherol (FIG. 11d).

Example 3

Separation of 2-ambo-α-tocopherol 2-ambo-α-tocopherol was analyzed by HPLC (Column: Daicel Chiracel® OD-H, 250 mm×4.6 mm; eluent 0.5% ethanol in n-heptane; flow 1 ml/min; detection 220 nm, 2 µl injection. FIG. 12b) shows this chromatogram (Retention time 7.2 resp. 8.2 min, 50.2:49.2).

140 mg 2-ambo-α-tocopherol in heptane were injected and two peaks with retention time at maximum of 13.4 min (1) (50.1%) and 15.0 min (2) (49.9%) were separated by the preparative HPLC separation. FIG. 12a) shows the chromatogram of the preparative HPLC separation.

After evaporation to dryness and dissolution the two collected fractions have been reanalysis on an analytical column (Daicel Chiracel® OD-H, 250 mm×4.6 mm; eluent 0.5% ethanol in n-heptane; flow 1 ml/min; detection 220 nm, 2 µl injection). FIG. 12c), respectively FIG. 12d), show the chromatogram of the first fraction, respectively the second fraction. The separation of the two isomers (Retention time 7.2 min, resp. 8.2 min) in the two fraction shows to be 99.5:0.5 (FIG. 12c)) resp. 0.8:99.2 (FIG. 12d). Hence, the two isomers have been separation by preparative chromatography almost completely.

The isomers have been identified to be (2R,4'R,8'R)-α-tocopherol (retention time 7.2 min) and (2S,4'R,8'R)-α-tocopherol (retention time 8.2 min).

2. Isomerization
Starting Materials:

Vitamin E compounds used for isomerization reactions were containing >99% of the (2R)-stereoisomer in all cases. (2R,4'R,8'R)-α-Tocopherol (Covitol® F1490, content min. 96%) was from Henkel (Lot 4C11504), and Cognis (Lot U40C03F002, (2R,4'R,8'R)-β-tocopherol, (2R,4'R,8'R)-γ-tocopherol, (2R,4'R,8'R)-δ-tocopherol, and (2R,4'R,8'R)-3,4-dehydro-α-tocopherol were prepared by chromatographic isolation and chemical modification from natural source material. Solvents and reagents used as received were acetonitrile (LiChrosolv Merck 1.00030), water (for chromatography Merck 1.15333), toluene (Fluka, 89681), n-heptane (Fluka, purum 51750, content 99%), ethylene carbonate (Aldrich, E26258, content 99.9%), p-toluenesulfonic acid monohydrate (Fluka, 89760), polytungstic acid hydrate (Aldrich 455970, content 88.9%).

Analytical Method
HPLC method 1:
Column: Daicel Chiracel® OD-H, 250 mm×4.6 mm; eluent 0.5% EtOH in n-hexane; flow 1 ml/min; detection 220 nm.

HPLC Method 2:
Column: Daicel Chiracel® OD-RH, 150 mm×4.6 mm, particle size 5 µm; eluent acetonitrile/water 80/20 (vol/vol); flow 1 ml/min; detection 210 nm; temp. 23° C.; retention times: (2R)-α-tocopherol 13.6 min, (2S)-α-tocopherol 15.7 min, (2R)-3,4-dehydro-α-tocopherol 17.7 min, (2S)-3,4-dehydro-α-tocopherol 21.4 min, (2R/2S)-6-hydroxy-2,5,7,8-tetramethyl-2-((4'RS,8'RS)-4,8,12-trimethyltridecyl)-chroman-4-one 13.8 min and 14.6 min.

Isomerization of (2R)-tocopherols to (2R/S)-tocopherols

Example 4

Isomerization of (2R,4'R,8'R)-α-tocopherol

To a magnetically stirred solution of (2R,4'R,8'R)-α-tocopherol (0.448 g, 96.2 wt %, 1.0 mmol) in toluene (10 ml) was added under an argon atmosphere p-toluenesulfonic acid monohydrate (0.19 g, 1.0 mmol). The solution was heated under reflux (bath temperature 140° C.) for 3 h. After cooling down to 25° C. the brown reaction mixture was diluted with n-hexane (25 ml) and washed successively with water (20 ml), saturated NaHCO$_3$-soln. (10 ml) and saturated NaCl-solution (10 ml), dried over MgSO$_4$, filtered and evaporated to dryness: 0.424 g yellowish oil, yield 95%, isomeric ratio 2R:2S=52.9:47.1 (determined by HPLC method 1). The chromatogram corresponds essentially to the chromatogram shown in FIG. 12b).

Example 4A

Isomerization of (2R,4'R,8'R)-α-tocopherol

To a solution of (2R,4'R,8'R)-α-tocopherol (4.44 g, 97.0 wt %, 10.0 mmol) in toluene (25 ml) was added at 41° C. under an argon atmosphere phosphotungstic acid hydrate (0.32 g, 0.1 mmol). The mixture was magnetically stirred under reflux (bath temperature 140° C., internal temp. 112-113° C.) for 4 h. After cooling down to 30° C. the brown reaction mixture was diluted with toluene (10 ml) and washed with saturated NaHCO$_3$-soln. (15 ml). The aqueous phase was extracted with toluene (5 ml), and the combined organic layers dried over Na$_2$SO$_4$ (10 g), filtered, the solid washed with toluene (5 ml), and the combined filtrate evaporated to dryness at 50° C./16 mbar/15 min and 25° C./0.1 mbar/16 h: 4.50 g brown oil, content 93.1 wt % α-tocopherol (GC, int. standard), isomeric ratio 2R:2S=51.7:48.3 (determined by HPLC method 2).

Example 4B

Isomerization of (2R,4'R,8'R)-α-tocopherol

To a mixture of (2R,4'R,8'R)-α-tocopherol (4.44 g, 97.0 wt %, 10.0 mmol), n-heptane (25 ml), and 25 g ethylene carbonate (molten at 50° C.) was added at 62° C. under an argon atmosphere phosphotungstic acid hydrate (0.65 g, 0.2 mmol). The mixture was magnetically stirred under reflux (bath temperature 140° C., internal temp. 105-106° C.) for 6 h. After cooling down to 80° C. the reaction mixture was transferred to a 100-ml separatory funnel. The upper yellow heptane phase was separated from the lower black ethylene carbonate phase at above 36° C. (melting point of ethylene carbonate). The lower phase was extracted with n-heptane (15 ml), the combined hexane extracts washed with saturated NaHCO$_3$-soln. (15 ml), and dried over Na$_2$SO$_4$ (10 g), filtered, the solid washed with n-heptane (2×5 ml), and the combined filtrate evaporated to dryness at 50° C./16 mbar/15 min and 25° C./0.1 mbar/16 h: 4.42 g brown oil, content 94.2 wt % α-tocopherol (GC, int. standard), isomeric ratio 2R:2S=53.7:46.3 (determined by HPLC method 2).

Example 5

Isomerization of (2R,4'R,8'R)-β-tocopherol

To a magnetically stirred solution of (2R,4'R,8'R)-β-tocopherol (0.417 g, 99.2 wt %, 1.0 mmol) in toluene (10 ml) was added under an argon atmosphere p-toluenesulfonic acid monohydrate (0.19 g, 1.0 mmol). The solution was heated under reflux (bath temperature 140° C.) for 14 h. After cooling down to 25° C. the brown reaction mixture was diluted with n-hexane (25 ml) and washed successively with water (20 ml), saturated NaHCO$_3$-soln. (10 ml) and saturated NaCl-solution (10 ml), dried over MgSO$_4$, filtered and evaporated to dryness: 0.378 g yellowish oil, isomeric ratio 2R:2S=51.5:48.5 (determined by HPLC method 1).

Example 6

Isomerization of (2R,4'R,8'R)-γ-tocopherol

To a magnetically stirred solution of (2R,4'R,8'R)-γ-tocopherol (0.428 g, 97.4 wt %, 1.0 mmol) in toluene (10 ml) was added under an argon atmosphere p-toluenesulfonic acid monohydrate (0.19 g, 1.0 mmol). The solution was heated under reflux (bath temperature 140° C.) for 3 h. After cooling down to 25° C. the brown reaction mixture was diluted with n-hexane (25 ml) and washed successively with water (20 ml), saturated NAHCO$_3$-soln. (10 ml) and saturated NaCl-solution (10 ml), dried over MgSO$_4$, filtered and evaporated to dryness: 0.424 g yellowish oil, isomeric ratio 2R:2S=47.8:52.2 (determined by HPLC method 1).

Example 7

Isomerization of (2R,4'R,8'R)-γ-tocopherol

To a mechanically stirred (550 rpm) solution of (2R,4'R, 8'R)-γ-tocopherol (43.94 g, 96.95 wt %, 102.25 mmol) in toluene (1000 ml) was added under an argon atmosphere p-toluenesulfonic acid monohydrate (19.65 g, 102.25 mmol). The solution was heated to reflux (bath temperature 140° C.) during ca. 1 h and stirred at this temperature for further 7 h. Chiral HPLC analysis of a sample showed completion of the isomerization (2R:2S=51:49) (determined by HPLC method 1) after 6.5 h reaction time. The mixture was cooled down, kept overnight at room temperature, evaporated in vacuo, taken up in n-hexane (500 ml), and filtered. The residue was washed with n-hexane (125 ml), and the combined filtrates washed three times with water (500 ml each), dried over MgSO$_4$, filtered, and evaporated to dryness: 41.21 g brown oil, yield 91.9%, purity 95.0 wt %, isomeric ratio 2R:2S=50.7:49.3. Further purification by column chromatography (2 kg silica gel 60, 0.063-0.2 mm, ethylacetate/n-hexane 1:9) and evaporation to dryness (40° C./16 mbar→23° C./0.3 mbar) gave 37.3 g brownish oil, yield 87.3%, purity 99.65 wt %, isomeric ratio 2R:2S=50.6:49.4.

FIG. 13 shows the chromatogram of the isomerized product of Example 7.

Example 8

Isomerization of (2R,4'R,8'R)-δ-tocopherol

To a solution of (2R,4'R,8'R)-δ-tocopherol (0.415 g, 96.96 wt %, 1.0 mmol) in toluene (10 ml) was added under an argon atmosphere p-toluenesulfonic acid monohydrate (0.19 g, 1.0 mmol). The solution was heated under reflux (bath temperature 140° C.) for 7 h. After cooling down to 25° C. the brown reaction mixture was diluted with n-hexane (25 ml) and washed successively with water (20 ml), saturated NaHCO$_3$-soln. (10 ml) and saturated NaCl-solution (10 ml), dried over MgSO₄, filtered and evaporated to dryness: 0.430 g yellowish oil, isomeric ratio 2R:2S=49.3:50.7 (determined by HPLC method 1).

Isomerization of dehydrotocopherols

Example 9

Isomerization of (2R,4'R,8'R)-3,4-dehydro-α-tocopherol (2R,4'R,8'R)-3,4-Dehydro-α-tocopherol (98.9 mg, 87.2 wt %, 0.201 mmol) was heated in a Kugelrohr oven under vacuum (ca. 11 mbar) for 7 h at 200° C. After cooling down to 25° C. the black oil was analyzed for the isomeric ratio, 2R:2S=51.0:49.0 (determined by HPLC method 1).

FIG. 14 shows the chromatogram of the isomerized product of Example 9.

Example 9A

Isomerization of (2R,4'R,8'R)-3,4-dehydro-α-tocopherol

To a solution of (2R,4'R,8'R)-3,4-dehydro-α-tocopherol (521 mg, 82.3 wt %, 1.0 mmol) in toluene (2.5 ml) was added at 34° C. under an argon atmosphere phosphotungstic acid hydrate (32 mg, 0.01 mmol). The mixture was magnetically stirred under reflux (bath temperature 140° C., internal temp. 112° C.) for 2 h. After cooling down to 25° C. the dark brown reaction mixture was diluted with toluene (3 ml) and washed with saturated NaHCO₃-soln. (5 ml). The organic layer was dried over Na₂SO₄ (2 g), filtered, the solid washed with toluene (5 ml), and the combined filtrate evaporated to dryness at 50° C./16 mbar/15 min and 25° C./0.1 mbar/1 h: 514 mg dark brown oil, isomeric ratio 2R:2S=50.3:49.7 (determined by HPLC method 2).

Example 9B

Isomerization of (2R,4'R,8'R)-3,4-dehydro-α-tocopherol

To a mixture of (2R,4'R,8'R)-3,4-dehydro-α-tocopherol (521 mg, 82.3 wt %, 1.0 mmol), n-heptane (2.5 ml), and 2.5 g ethylene carbonate (molten at 50° C.) was added at 44° C. under an argon atmosphere phosphotungstic acid hydrate (65 mg, 0.02 mmol). The mixture was magnetically stirred under reflux (bath temperature 140° C., internal temp. 101° C.) for 2.5 h. After cooling down to 60° C. the black two-phasic reaction mixture was transferred to a separatory funnel. A saturated NaHCO₃-soln. (5 ml) was added, and the mixture extracted with n-heptane (3 ml). The upper heptane phase was separated and dried over Na₂SO₄ (2 g), filtered, the solid washed with n-heptane (5 ml), and the combined filtrate evaporated to dryness at 50° C./16 mbar/15 min and 25° C./0.1 mbar/1 h: 509 mg dark brown oil, isomeric ratio 2R:2S=49.0:51.0 (determined by HPLC method 2).

3. Separation Quality

The following experiments relate to the quality of chromatographic separation of isomers of (all-rac)-α-tocopherol (DSM Nutritional Products) (100 mg/ml) by means of chiral phases (Daicel Chiralpak® IA (3 µm), 250 mm×4.6 mm) using different eluents flow 1 ml/min; detection 280 nm).

FIG. 15 shows the separation of isomers using different alcohols in the eluent. In all cases 5 µl corresponding to an absolute amount of 0.5 mg (all-rac)-α-tocopherol have been injected.

| Example | Example 10a) | Example 10b) | Example 10c) |
|---|---|---|---|
| Heptane | 99.5% (v/v)) | 98% (v/v)) | 98% (v/v)) |
| Alcohol | Ethanol 0.5% (v/v)) | Isopropanol 2% (v/v)) | 1-propanol 2% (v/v)) |
| Chromatogram: | FIG. 15 a) | FIG. 15 b) | FIG. 15 c) |

The comparison shows that kind of alcohol has a strong influence on the quality of separation of the isomers. FIG. 15 c) shows that particularly 1-propanol shows a preferentially good separation quality.

FIG. 16 shows the beneficial effect of an organic acid (S1) with a pK$_a$ of less than 6.0 in the eluent. In all cases 5 µl corresponding to an absolute amount of 0.5 mg (all-rac)-α-tocopherol have been injected.

| Example | Example 11a) | Example 11b) | Example 11c) | Example 11d) |
|---|---|---|---|---|
| Heptane | 99.5% (v/v)) | 99.3% (v/v)) | 98% (v/v)) | 98.8% (v/v)) |
| Alcohol | Ethanol 0.5% (v/v)) | Ethanol 0.5% (v/v)) | 1-propanol 2% (v/v)) | 1-propanol 1% (v/v)) |
| Organic acid | | Acetic acid 0.2% (v/v)) | | Acetic acid 0.2% (v/v)) |
| Chromatogram: | FIG. 16 a) | FIG. 16 b) | FIG. 16 c) | FIG. 16 d) |

FIG. 17 shows the beneficial effect of combination of alcohol and organic acid (S1) with a pK$_a$ of less than 6.0 in the eluent on the loadability. Different amounts have been injected.

| Example | Example 12a) | Example 12b) | Example 12c) | Example 12d) |
|---|---|---|---|---|
| Heptane | 99.5% (v/v)) | 99.5% (v/v)) | 98.8% (v/v)) | 98.8% (v/v)) |
| Alcohol | Ethanol 0.5% (v/v)) | Ethanol 0.5% (v/v)) | 1-propanol 1% (v/v)) | 1-propanol 1% (v/v)) |
| Organic acid | | | Acetic acid 0.2% (v/v)) | Acetic acid 0.2% (v/v)) |
| Amount injected | 5 µl 0.5 mg | 10 µl 1 mg | 5 µl 0.5 mg | 25 µl 2.5 mg |
| Chromatogram: | FIG. 17 a) | FIG. 17 b) | FIG. 17 c) | FIG. 17 d) |

The comparison shows that in case of ethanol (FIG. 17a) and b)) the two peaks overlap already considerably at relative low amounts of isomer mixture injected to the column, whereas in case of 1-propanol and acetic acid (FIG. 17c) and d)) the separation is much better and excellent separation can be obtained at even much higher amounts injected isomer mixture injected to the column.

The invention claimed is:

1. A process of separating chiral isomers of formula (I-A) or (I-B) or (I-C):

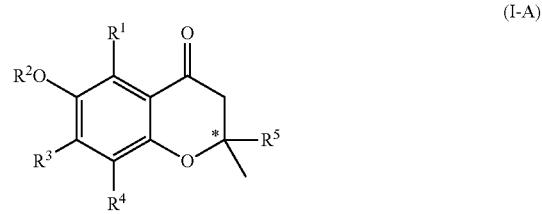

(I-A)

-continued

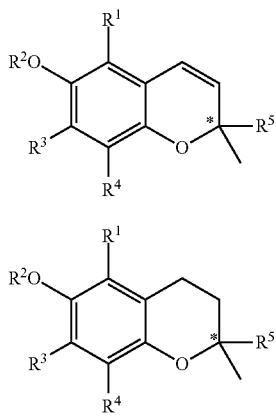

wherein $R^1$, $R^3$ and $R^4$ are independently from each other hydrogen or methyl groups;
$R^2$ represents hydrogen or an phenol protection group;
$R^5$ represents either a linear or branched completely saturated $C_{6-25}$-alkyl group or a linear or branched $C_{8-25}$-alkyl group comprising at least one carbon-carbon double bond;
and wherein * represents the chiral centre of the chiral isomer of formula (I-A) or (I-B) or (I-C);
the process comprising the steps of:
a) providing a mixture of at least two isomers of formula (I-A) or (I-B) or (I-C);
b) performing chromatographic separation of the mixture of isomers of formula (I-A) or (I-B) or (I-C) by means of a chiral phase into desired isomer (I) and residual (I');
c) isomerizing the chirality at the centre indicated by * in formula (I-A) or (I-B) or (I-C) of the isomers of the residual (I') being separated in step b);
d) adding the isomerized isomers obtained in step c) to a mixture of at least two isomers of formula (I-A) or (I-B) or (I-C) being object of further separation; and
e) collecting the desired isomer (I).

2. The process according to claim 1, wherein the isomerisation of step c) is practiced by exposing the residual (I') to a temperatures above 150° C.

3. The process according to claim 1, wherein the isomerisation of step c) is practiced by exposing the residual (I') to an acid of a $pK_a$ of smaller than 2.

4. The process according to claim 1, wherein the acid having a $pK_a$ of smaller than 2 is p-toluenesulphonic acid.

5. The process according to claim 1, wherein the isomerisation of step c) is practiced by exposing the residual (I') to a base of which the corresponding acid has a $pK_a$ of larger than 13.

6. The process according to claim 1, wherein the process is a continuous process.

7. The process according to claim 1, wherein $R^5$ is of formula (II):

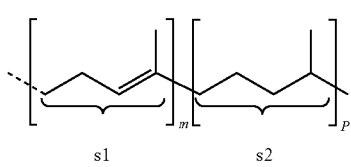

wherein m and p stand independently from each other for a value of 0 to 5 provided that the sum of m and p is 1 to 5, and where
the substructures in formula (II) represented by s1 and s2 can be in any sequence; and
the dotted line represents the bond by which the substituent of formula (II) is bound to the rest of formula (I-A) or (I-B) or (I-C).

8. The process according to claim 1, wherein $R^1=R^3=R^4=CH_3$ or $R^1=R^4=CH_3, R^3=H$ or $R^1=H, R^3=R^4=CH_3$ or $R^1=R^3=H, R^4=CH_3$.

9. The process according to claim 1, wherein $R^2$ is H.

10. The process according to claim 1, wherein the desired chiral isomers of formula (I-A) or (I-B) or (I-C) has the R-configuration at the carbon marked by * in formula (I-A) or (I-B) or (I-C).

11. The process according to claim 1, wherein the desired chiral isomers of formula (I-A) or (I-B) or (I-C) are the isomers of a tocotrienol or the acetate thereof.

12. The process according to claim 1, wherein the desired chiral isomers of formula (I-A) or (I-B) or (I-C) are the isomers (2R, 4'R, 8'R)-α-tocopherol or (2R, 4'R, 8'R)-α-tocopheryl acetate.

13. The process according to claim 1, wherein the desired chiral isomer is tocopherol or tocopheryl acetate respectively obtained from tocotrienol or tocotrienyl acetate, by a step of asymmetrical hydrogenation using a chiral iridium complex which takes place either before step b) or after step e).

14. The process according to claim 1, wherein the chiral phase is a chiral phase of the group consisting of celluloses, amyloses, dextrans, cyclodextrines and derivatives thereof.

15. The process according to claim 1, wherein the chiral chromatographic separation uses a Simulated Moving Bed (SMB) chromatography.

16. The process according to claim 1, wherein the chromatographic separation in step b) is in presence of at least one alcohol.

17. The process according to claim 1, wherein the chromatographic separation of step b) is practiced in the presence of at least an organic acid with a $pK_a$ of less than 6.0.

18. The process according to claim 2, wherein the isomerisation of step c) is practiced by exposing the residual (I') to a temperatures between 160 and 500° C.

19. The process according to claim 18, wherein the isomerisation of step c) is practiced by exposing the residual (I') to a temperatures between 160 and 300° C.

20. The process according to claim 3, wherein the $pK_a$ of the acid is smaller than 1.

21. The process according to claim 11, wherein the desired chiral isomers of formula (I-A) or (I-B) or (I-C) are the isomers of (2R)-tocotrienol or the acetated thereof.

22. The process according to claim 21, wherein the desired chiral isomers of formula (I-A) or (I-B) or (I-C) are the isomers of (2R)-α-tocotrienol or the acetate thereof.

23. The process according to claim 16, wherein the at least one alcohol is selected from the group consisting of methanol, ethanol, 1-propanol, 2-propanol, 1-butanol, isobutanol, tert.-butanol, 2-methyl-2-butanol, 3-methyl-2-butanol, 3-methyl-1-butanol, 2-methyl-1-butanol and allylalcohol.

24. The process according to claim 23, wherein the at least one alcohol is 1-propanol.

25. The process according to claim 17, wherein the chromatographic separation of in step b) is practiced in the presence of at least an organic acid with a $pK_a$ of between 3.0 and 6.0.

26. The process according to claim 25, wherein the organic acid is acetic acid.

* * * * *